Figure 1:
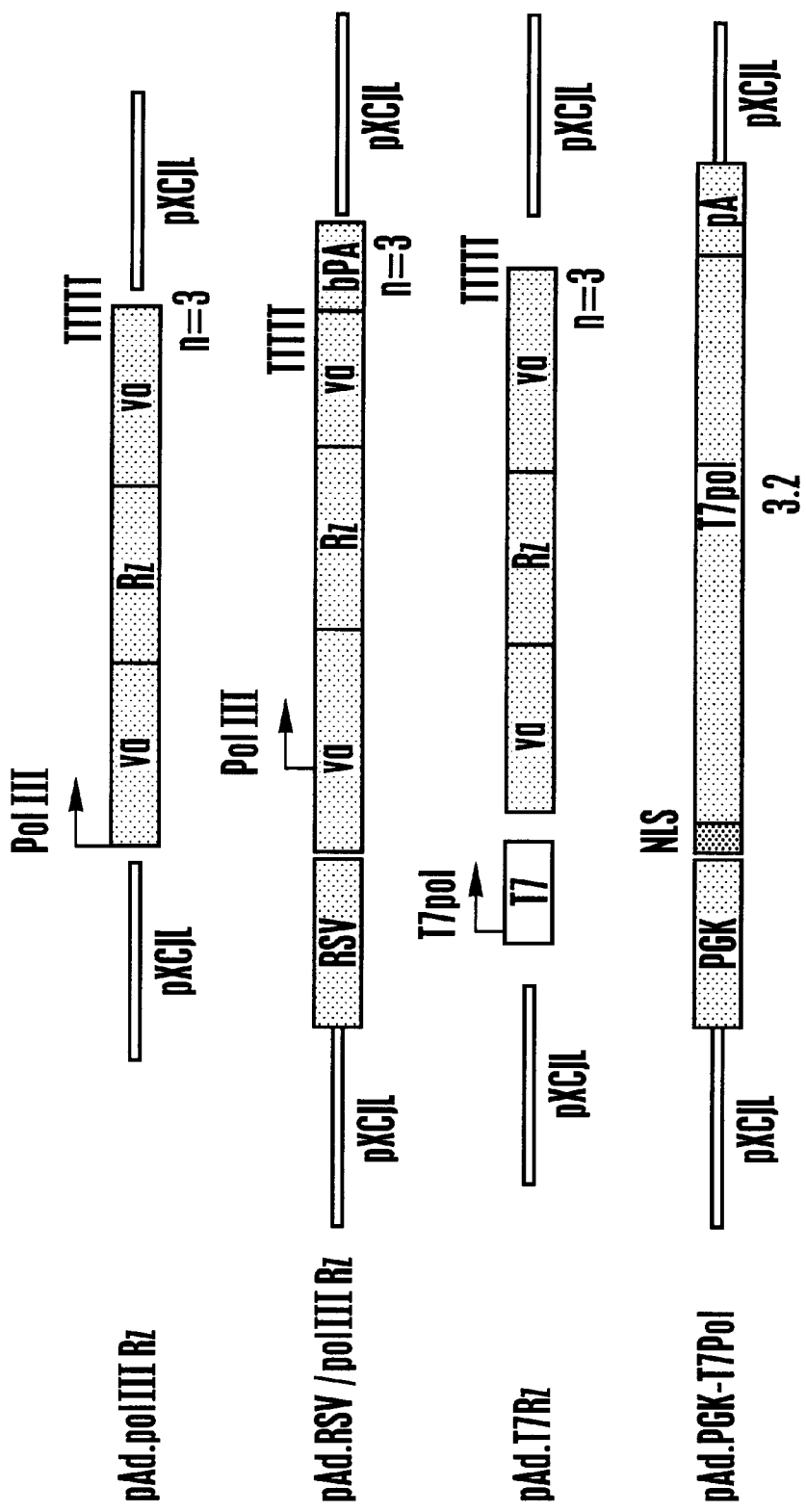

United States Patent [19]
Kay et al.

[11] Patent Number: 6,107,028
[45] Date of Patent: *Aug. 22, 2000

[54] RIBOZYMES FOR TREATING HEPATITIS C

[75] Inventors: Mark A. Kay; Andre Lieber, both of Seattle, Wash.

[73] Assignee: University of Washington, Seattle, Wash.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/648,272

[22] Filed: May 15, 1996

Related U.S. Application Data

[63] Continuation-in-part of application No. 08/534,220, Sep. 11, 1995, which is a continuation-in-part of application No. 08/476,257, Jun. 7, 1995, abandoned, which is a continuation-in-part of application No. 08/357,508, Dec. 14, 1994, abandoned.

[51] Int. Cl.[7] .............................. C07H 21/04; C12Q 1/68; C12N 15/63; A61K 48/00
[52] U.S. Cl. ...................... 435/6; 435/91.31; 435/320.1; 435/366; 435/370; 536/23.1; 536/24.5
[58] Field of Search ..................... 435/6, 91.31, 172.1, 435/172.3, 320.1, 366, 358, 365, 370; 536/23.1, 23.2, 24.5; 514/44

[56] References Cited

U.S. PATENT DOCUMENTS

| | | | |
|---|---|---|---|
| 4,861,719 | 8/1989 | Miller | 435/236 |
| 4,987,071 | 1/1991 | Cech et al. | 435/91.31 |
| 5,124,263 | 6/1992 | Temin et al. | 435/349 |
| 5,219,740 | 6/1993 | Miller et al. | 435/69.6 |
| 5,350,671 | 9/1994 | Houghton et al. | 435/5 |
| 5,354,855 | 10/1994 | Cech et al. | 536/24.1 |
| 5,399,346 | 3/1995 | Anderson et al. | 424/93.21 |
| 5,436,146 | 7/1995 | Shenk et al. | 435/457 |
| 5,610,054 | 3/1997 | Drapes et al. | 435/363 |

FOREIGN PATENT DOCUMENTS

| | | |
|---|---|---|
| 0558944 | 9/1993 | European Pat. Off. . |
| 2 212 511 | 7/1989 | United Kingdom . |
| WO 92/12242 | 7/1992 | WIPO . |
| 9323569 | 11/1993 | WIPO . |
| WO 94/02601 | 2/1994 | WIPO . |
| WO 94/20146 | 9/1994 | WIPO . |
| WO 94/26915 | 11/1994 | WIPO . |
| WO 94/27556 | 12/1994 | WIPO . |
| WO 94/29471 | 12/1994 | WIPO . |
| WO 95/19429 | 7/1995 | WIPO . |
| WO 96/01314 | 1/1996 | WIPO . |
| WO 96/01315 | 1/1996 | WIPO . |

OTHER PUBLICATIONS

Grundmann et al., *Liver Regeneration After Experimental Injury* Lesch & Reuter (eds.), NY: Stratton Intercontinental Medical Book Co. (1973).

Guerrier–Takada et al., "The RNA Moiety of Ribonuclease P is the Catalytic Subunit of the Enzyme," *Cell* 35:849 (1983).

Hampel et al., "RNA Catalytic Properties of the Minimum (–)sTRSV Sequence," *Biochem.* 28:4929–4933 (1989).

Hampel et al., "'Hairpin' Catalytic RNA Model: Evidence for Helices and Sequence Requirement for Substrate RNA," *Nucl. Acids Res.* 18(2):299–304 (1990).

Heckel et al., "Neonatal Bleeding in Transgenic Mice Expressing Urokinase–Type Plasminogen Activator," *Cell* 62:447–456 (1990).

Hofmann et al., "Efficient Gene Transfer into Human Hepatocytes by Baculorivus Vectors," *Proc. Natl. Acad. Sci. USA* 92:10099–10103 (1995).

Kay et al., "Hepatic Gene Therapy: Persistent Expression of Human α1–Antitrypsin in Mice after Direct Gene Delivery In Vivo," *Hum. Gene Ther.* 3:641–647 (1992).

Kay et al., "In vivo Hepatic Gene Therapy: Complete Albeit Transient Correction of Factor IX Deficiency in Hemophilia B Dogs," *Proc. Natl. Acad. Sci. USA* 91:2353–2357 (1994).

Kay et al., "In Vivo Gene Therapy of Hemophilia B: Sustained Partial Correction in Factor IX–Deficient Dogs," *Sci.* 262:117–119 (1993).

Ledley et al., "Hepatic Gene Therapy: Present and Future," *Hepatol.* 18(5):1263–1273 (1993).

Li et al., "Assessment of Recombinant Adenoviral Vectors for Hepatic Gener Therapy," *Human Gene Ther.* 4:403–409 (1993).

Miller, "Progess Toward Human Gene Therapy," *Blood* 76:271–278 (1990).

Miller et al., "Gene Transfer by Retrovirus Vectors Occurs Only in Cells That are Actively Replicating at the Time of Infection," *Mol. Cell. Biol.* 10:4239–4242 (1990).

Miller, "Human Gene Therapy Comes of Age," *Nature* 357:455–460 (1992).

(List continued on next page.)

*Primary Examiner*—David Guzo
*Assistant Examiner*—Andrew Wang
*Attorney, Agent, or Firm*—Campbell & Flores LLP

[57] ABSTRACT

A method of inhibiting hepatitis C virus RNA replication or expression is provided. The method consists of introducing two or more ribozymes specific for hepatitis C virus RNA into a cell infected with hepatitis C virus. The ribozymes specific for hepatitis C virus RNA can specifically cleave hepatitis C RNA in a HCV 5' non-coding sequence, the capsid sequence, the NS-5 sequence or any other conserved region of the hepatitis C RNA. The ribozymes can also be selected so as to be specific for opposite strands of the virus genome. A method of inhibiting hepatitis C virus RNA replication or expression is also provided which consists of introducing into a cell infected with hepatitis C virus at least one ribozyme specific for hepatitis C virus which is selected from the group consisting of GGGAGGTCTCGTAGA [SEQ ID NO: 1], GCACCATGAGCACGA [SEQ ID NO: 2], CCCACAGGACGTCAA [SEQ ID NO: 3], CAAC-CGTCGCCCACA [SEQ ID NO: 4], TAAACCTCAAA-GAAA [SEQ ID NO: 5] GTAAGGTCATCGATA [SEQ ID NO: 6]. Compositions consisting of two or more ribozymes specific for hepatitis C virus RNA is also provided.

38 Claims, 10 Drawing Sheets

OTHER PUBLICATIONS

Nagai et al., "Molecular Cloning of cDNA Coding for Human Preprourokinase," *Gene* 36:183–188 (1985).

Okamoto et al., "Full–Length Sequence of a Hepatitis C Virus Genome Having Poor Homology to Reported Isolates: Comparative Study of Four Distinct Genotypes," *Virol.* 188:331–341 (1992).

Pelham, "Evidence that Luminal ER Proteins are Sorted From Secreted Proteins in a Post–ER Compartment," *EMBO J.* 7:913–918 (1988).

Perrotta and Been, "Cleavage of Oligoribonucleotides by a Ribozyme Derived from the Hepatitis δ Virus RNA Sequence," *Biochem.* 31:16–21 (1992).

Pozzato et al., "Different Genotypes of Hepatitis C Virus are Associated With Different Severity of Chronic Liver Disease," *J. Med. Virol.* 43:291–296 (1994).

Rhim et al., "Replacement of Diseased Mouse Liver by Hepatic Cell Transplantation," *Sci.* 263:1149–1152 (1994).

Rossi et al., "Ribozymes as Anti–HIV–1 Therapeutic Agents: Principles, Applications, and Problems," *AIDS Res. Hum. Retrovir.* 8:183 (1992).

Sandgren et al., "Complete Hepatic Regeneration After Somatic Deletion of an Albumin–Plasminogen Activator Transgene," *Cell* 66:245–256 (1991).

Schutze et al., "An N–terminal Double–Arginine Motif Maintains Type II Membrane Proteins in the Endoplasmic Reticulum," *EMBO J.* 13:1696–1705 (1994).

Shenk et al., "Genetic Analysis of Adenoviruses," *Curr. Top. Microbiol. Immunol.* 111:1–39 (1984).

Stratford–Perricaudet et al., "Widespread Long–term Gene Transfer to Mouse Skeletal Muscles and Heart," *J. Clin. Invest.* 90:626–630 (1992).

Strubin et al., "Two Forms of the Ia Antigen–Associated Invariant Chain Result from Alternative Initiations at Two In–Phase AUGs," *Cell* 47:619–625 (1986).

Yang et al., "Cellular Immunity to Viral Antigens Limits E1–deleted Adenoviruses for Gene Therapy," *Proc. Natl. Acad. Sci. USA* 91:4407–4411 (1994).

Yoshioka et al., "Detection of Hepatitis C Virus by Polymerase Chain Reaction and Response to Interferon–α Therapy: Relationship to Genotypes of Hepatitis C Virus," *Hepatol.* 16:293–299 (1992).

Barr et al., "Strain Related Variations in Adenovirally Mediated Transgene Expression from Mouse Hepatocytes In Vivo: Comparisons Between Immunocompetent and Immunodeficient Inbred Strains," *Gene Ther.* 2:151–155 (1995).

Cech, "Ribozyme Engineering," *Curr. Op. Structural Biol.* 2:605–609 (1992).

Fausto, "Hepatocyte Differentiation and Liver Progenitor Cells," *Curr. Op. Cell Biol.* 2:1096–1042 (1990).

Frankel (ed.), *Genetically Engineered Toxins*, Marcel Dekker, Inc. (1992).

Gorlich et al., "A Protein of the Endoplasmic Reticulum Involved Early in Polypeptide Translocation," *Nature* 357:47–52 (1992).

Grable et al., "cis and trans Requirements for the Selective Packaging of Adenovirus Type 5 DNA," *J. Virol.* 66:723–731 (1992).

Graham and Prevec, "Manipulation of Adenovirus Vectors," *Methods in Molecular Biology: Gene Transfer and Expression Protocols*, The Humana Press 7:109–128 (1991).

Stull et al. Pharm Res 12:465–483 (1995).

Sokol et al. Transgenic Research 5:363–371 (1996).

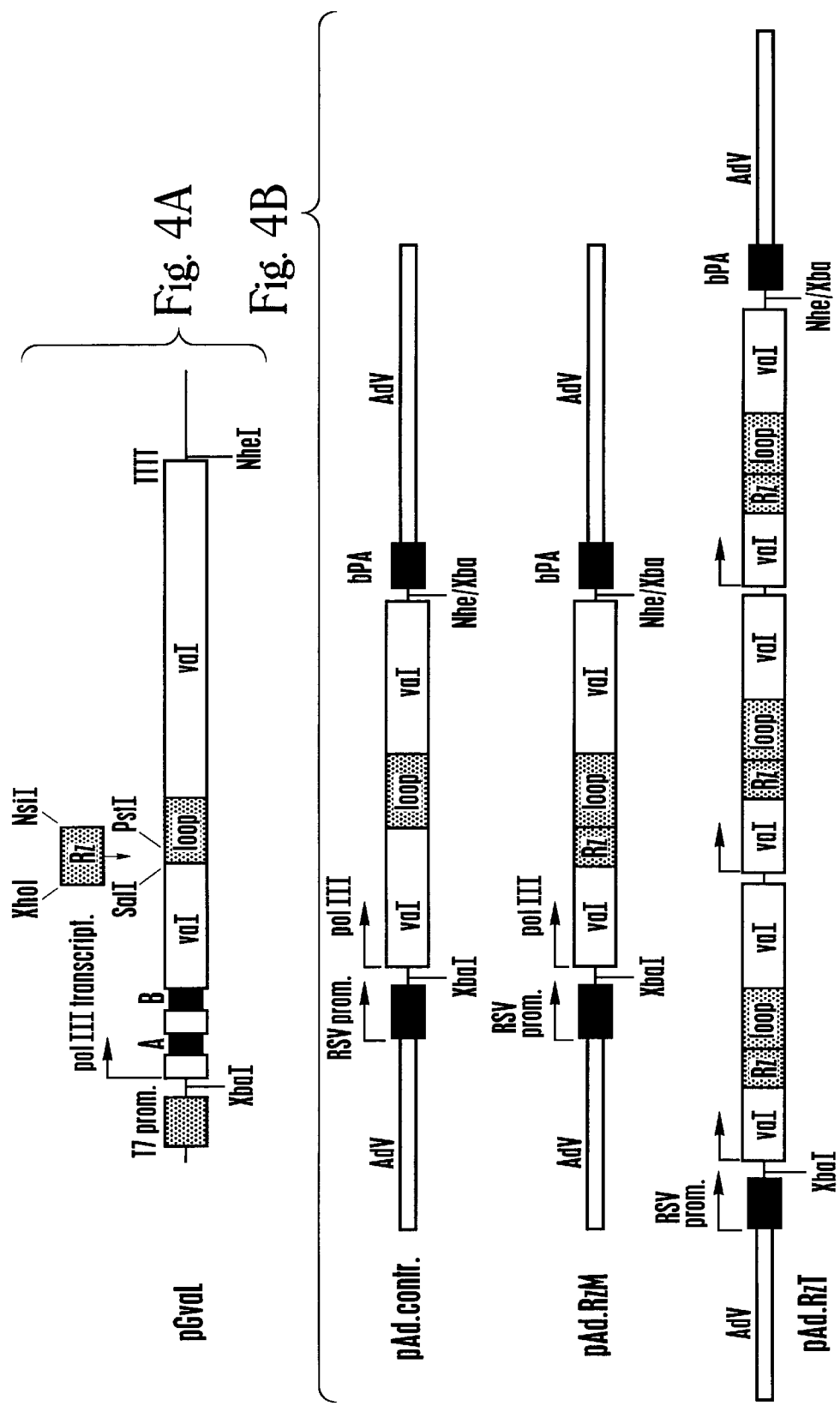

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:1:

GGGAGGTCTC GTAGA                                                15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:2:

GCACCATGAG CACGA                                                15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:3:

CCCACAGGAC GTCAA                                                15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:4:

CAACCGTCGC CCACA                                                15

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:5:

TAAACCTCAA AGAAA                                                15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single (D) TOPOLOGY: linear (xi) SEQUENCE DESCRIPTION: SEQ ID NO:6:

GTAAGGTCAT CGATA                                                    15

(2) INFORMATION FOR SEQ ID NO:7:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:7:

CGTCGACTGC TGCAGTGCAG CGTGTGGACC CAACGACACG CGGGCGGTAA CCGACGT      57

(2) INFORMATION FOR SEQ ID NO:8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:8:

CGGTTACCGC CCGCGTGTCG TTGGGTCCAC ACGCTGCACT GCAGCAGTCG ACGACGT      57

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:9:

CCGCTCGAGN NNNNNNNNNN NNCTGATGAG TCCGTGAGGA CGAAA                   45

(2) INFORMATION FOR SEQ ID NO:10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 21
        (D) OTHER INFORMATION: /note= "N=NG, where NG is 40% C;
            40% G; 10% T, and 10% A."

(xi) SEQUENCE DESCRIPTION: SEQ ID NO:10:

TGCATGCATN NNNNNNNNNN NTTTCGTCCT CACGGACTCA TCAG                    44

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:11:

GAGAATTCTA GAGGATCCCC CCCCCCCC                                      28

(2) INFORMATION FOR SEQ ID NO:12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:12:

GAGAATTCCA AGGCCAGGAG AGGCACTGGG GA                                32

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

GTAAACTCCA CCAACGATCT                                              20

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:14:

GAAGATAGAG AAAGAGCA                                                18

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:15:

ACCCCATGAG GTCGGCGAA                                               19

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:16:

CTGTGAGGAA CTACTGT                                                 17

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

CACGCAGAAA GCGTCTAGCC                                              20

(2) INFORMATION FOR SEQ ID NO:18:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:18:

CGTCTAGAGC CAGCCCCCTG ATGGGG                                              26

(2) INFORMATION FOR SEQ ID NO:19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (xi) SEQUENCE DESCRIPTION: SEQ ID NO:19:

AAGGGTACCC GGGCTGAGC                                                      19

(2) INFORMATION FOR SEQ ID NO:20:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:20:

TGACGTCCTG TGGGCGACGG TTGGTG                                              26

(2) INFORMATION FOR SEQ ID NO:21:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:21:

AGCCGAGTAG TGTTGGGTCG CGAAAGG                                             27

(2) INFORMATION FOR SEQ ID NO:22:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:22:

AGCGGCCGGA GAACCTGCGT GCAATC                                              26

(2) INFORMATION FOR SEQ ID NO:23:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:23:

TCGTTGGGTC CACACGCTGC ACTGCAT                                             27

(2) INFORMATION FOR SEQ ID NO:24:

(i) SEQUENCE CHARACTERISTICS:

-continued

```
    (A) LENGTH: 29 base pairs
    (B) TYPE: nucleic acid
    (C) STRANDEDNESS: single
    (D) TOPOLOGY: linear (xi) SEQUENCE DESCRIPTION: SEQ ID NO:24:

TGTTGAAGGT TGGGTGATCC TGATCATGG                                29
```

RIBOZYMES FOR TREATING HEPATITIS C

This application is a continuation-in-part of U.S. Ser. No. 08/534,220 filed Sep. 11, 1995, which is a continuation-in-part of U.S. Ser. No. 08/476,257, filed Jun. 7, 1995, now abandoned, which is a continuation-in-part of U.S. Ser. No. 08/357,508, filed Dec. 14, 1994, now abandoned. The contents of all such related applications are incorporated herein by reference in their entirety.

Certain embodiments of the invention described herein were made in the course of work supported by the National Institutes of Health pursuant to grant no. DK47754. Therefore, the U.S. Government has certain rights in this invention.

BACKGROUND OF THE INVENTION

The major etiological agent of posttransfusional and community acquired non-A non-B hepatitis has been identified as hepatitis C virus (HCV). Choo et al., *Science* 244:359–362 (1989). At present, intravenous drug abuse is the most important risk factor for transmission of HCV. However, different epidemiological studies have revealed that for up to 20 to 40% of patients chronically infected with HCV, no known risk factors for HCV can be demonstrated. Alter et al., *N. Engl. J. Med.* 327:1899–1905 (1992).

Although the disease associated with HCV may be benign, persistent infection may lead to liver cirrhosis and hepatocellular carcinoma (Saito et al., *Proc. Natl. Acad. Sci. USA* 87:6547–6549), although the mechanism of cellular transformation is unknown. HCV disease can be manifested as acute viral hepatitis which is usually clinically mild, but in other cases the disease may develop into a severe or fulminant hepatitis. Chronic HCV hepatitis is believed to occur more frequently than with hepatitis B virus, especially following posttransfusional acute hepatitis C disease, i.e., in about 54% of cases. Hollinger, in *Fields Virology*, 2d ed., Chpt. 78, eds. B. Fields and D. Knipe, Raven Press, NY (1990).

On the basis of sequence homology, the single-stranded positive-sense RNA enveloped HCV virus has been provisionally classified as a separate genus of the family Flaviviridae. Miller and Purcell, *Proc. Natl. Acad. Sci. USA* 87:2057–2061 (1990). The HCV genome is about 10 kb in length and it encodes a single polyprotein of about 3,000 amino acids that includes structural and nonstructural proteins that are processed by cellular and virus-encoded proteinases. The processed gene products include a putative capsid (C), three putative envelopes (E1, E2 type A, and E2 type B), and six nonstructural (NS) proteins (NS2, NS3, NS4A, NS4B, NS5A, and NS5B). Representative sequences of HCV strains are described in U.S. Pat. No. 5,350,671 to Houghton et al., incorporated herein by reference.

Comparative sequence analysis of complete HCV genomes (Okamoto et al., *Virology* 188:331–341 (1992)) and PCR fragments from various genomic regions has shown that HCV may be grouped into distinct but related genotypes. At present, six major genotypes (1–6) with numerous subtypes (e.g., 1a, 1b; 2a, 2b, 3a, 5a) have been identified. Three additional types have been recently identified but are apparently limited in geographic distribution. Some genotypes have been associated with severity of disease (Pozzato et al., *J. Med. Virol.* 43:291–296 (1994)) and responsiveness to interferon therapy (Yoshioka et al., *Hepatology* 16:293–299 (1992)).

To date, treatment of HCV infection has primarily been with alpha-interferon. In some instances liver transplantation has been performed for end-stage hepatic deficiency, but invariably the transplanted liver also becomes infected with HCV and ultimately fails.

Gene therapy involves the introduction of genetic material into the cells of an organism to treat or prevent a disease. The material transferred can be from a few nucleotides to a few genes in size. Gene therapy is potentially useful in the treatment and prevention of acquired diseases, such as infectious diseases and cancer. A variety of cell types have been targeted in somatic cell gene therapy systems, including hematopoietic cells, skin fibroblasts and keratinocytes, hepatocytes, endothelial cells, skeletal and smooth muscle cells, and lymphocytes, each with varying success.

Methods for gene therapy involving hepatocytes have relied on gene transfer ex vivo, i.e., inserting genes into hepatocytes which have been removed from a patient which are then reimplanted into the liver, or in vivo, i.e., gene transfer directly into the liver. For ex vivo methods, gene transfer into cells must occur at high efficiency to obtain suitable numbers of cells for transplantation, because primary cultures of hepatocytes cannot be expanded. Long term expression in transduced hepatocytes has been accomplished with retroviral vectors, but the efficiency of transduction is relatively low (the retrovirus infects only dividing cells; Miller et al., *Mol. Cell. Biol.* 10:4239–4242 (1990)), and the protein may not be expressed in therapeutically or prophylactically effective amounts. In one ex vivo method approximately 20% of a patient's liver is surgically removed, the cells are then transduced with the retroviral vector, and then implanted back into the patient. This approach suffers from obvious disadvantages of surgical procedures and a low efficiency of transduction and expression of the gene product of interest.

Similarly, an in vivo approach to transducing hepatocytes with retroviral vectors involves first performing a partial hepatectomy followed by portal vein infusion of the vector. The removal of the majority of the liver is needed to stimulate liver regeneration so that the retrovirus will integrate into the cells' genomes. As with the ex vivo approach, this method suffers from requiring a major surgical procedure and under the best of conditions only about 1% of the liver mass contains the genetically modified vectors.

As an alternative to retroviral-mediated hepatic gene therapy, the adenovirus presents a transfer vector that can infect nonreplicating cells at high efficiency. Adenoviral DNA remains extra-chromosomal and thus is slowly lost from transduced hepatocytes over a period of several months. Li et al., *Human Gene Ther.* 4:403–409 (1993); Kay et al., *Proc. Natl. Acad. Sci. USA* 91:2353–2357 (1994). Additionally, a substantial portion of the adenovirus is taken up by organs and tissues other than the liver, which may raise issues of safety. (Smith et al., 1993, and Kay et al., ibid.). And, as adenovirus stimulates the production of neutralizing antibodies in an infected host, patients who have been naturally infected with adenovirus may be resistant to gene therapy using this vector, or secondary transductions may be prevented by the presence of antibodies produced in response to a primary transduction (Smith ibid., Kay, ibid.).

There remains a significant need in the art for compositions useful in treating hepatitis C infection and methods for their delivery to HCV-infected cells of the liver. Desirably, the compositions and methods should effectively reduce or eradicate HCV from infected cells, or should significantly impair the ability of the virus to replicate, thereby preventing further dissemination of the disease. The compositions should be inherently specific for HCV and of negligible toxicity. Quite surprisingly, the present invention fulfills these and other related needs.

SUMMARY OF THE INVENTION

Methods and compositions are provided for producing ribozymes targeted to HCV gene products of interest in an HCV-infected or susceptible mammal, thereby inhibiting or preventing HCV infection and spread. In one aspect, a method of inhibiting hepatitis C virus RNA replication or expression is provided. The method consists of introducing two or more ribozymes specific for hepatitis C virus RNA into a cell infected with hepatitis C virus. The ribozymes specific for hepatitis C virus RNA can specifically cleave hepatitis C RNA in a HCV 5' non-coding sequence, the capsid sequence, the NS-5 sequence or any other conserved region of the hepatitis C RNA. The ribozymes can also be selected so as to be specific for opposite strands of the virus genome. A method of inhibiting hepatitis C virus RNA replication or expression is also provided which consists of introducing into a cell infected with hepatitis C virus at least one ribozyme specific for hepatitis C virus which is selected from the group consisting of GGGAGGTCTCGTAGA [SEQ ID NO: 1], GCACCATGAGCACGA [SEQ ID NO: 2], CCCACAGGACGTCAA [SEQ ID NO: 3], CAACCGTCGCCCACA [SEQ ID NO: 4], TAAACCTCAAAGAAA [SEQ ID NO: 5] GTAAGGTCATCGATA [SEQ ID NO: 6]. Compositions consisting of two or more ribozymes specific for hepatitis C virus RNA is also provided.

In another aspect the methods comprise transducing cells, especially hepatocytes, with a recombinant adenovirus which encodes a ribozyme specific for hepatitis C virus RNA. When the sequence encoding the ribozyme is expressed, HCV RNA in the infected cell is inhibited or infection is prevented. Preferably the ribozyme is a hammerhead ribozyme, and specifically cleaves hepatitis C RNA in a HCV 5' non-coding sequence, capsid sequence, the NS-5 sequence or any other conserved region of the hepatitis C RNA. Administration may be performed with hepatocytes from an HCV-infected individual, i.e., ex vivo administration, or administered to the individual. When administered to an individual, typically administration will be by infusion, such as via the portal vein or bile duct. Typically the recombinant adenovirus is administered to the hepatocytes in an amount and for a time sufficient to eradicate hepatitis C virus from the hepatocytes, preferably from about 10 to 100 adenovirus particles per hepatocyte. For increased activity against HCV, the vector(s) may encode two or more ribozymes specific for different regions or strands of HCV RNA.

In yet another aspect the invention provides recombinant adenovirus encoding at least one ribozyme specific for HCV RNA, and sometimes will encode two or more different ribozymes specific for HCV RNA. Preferably the recombinant adenovirus encodes a hammerhead ribozyme specific for HCV. In yet other embodiments a ribozyme specific for HCV RNA targets an HCV sequence that corresponds to a cDNA sequence comprising GGGAGGTCTCGTAGA [SEQ ID NO: 1] (nucleotide 318 to 332), GCACCATGAGCACGA [SEQ ID NO: 2] (nucleotide 335 to 349), CCCACAGGACGTCAA [SEQ ID NO: 3] (nucleotide 395 to 409), CAACCGTCGCCCACA [SEQ ID NO: 4] (nucleotide 386 to 400), TAAACCTCAAAGAAA [SEQ ID NO: 5] (nucleotide 358–370) or GTAAGGTCATCGATA [SEQ ID NO: 6] (nucleotide 699 to 714).

BRIEF DESCRIPTION OF THE FIGURES

FIG. 1 shows adenovirus ribozyme expression cassettes. The ribozymes are cloned into the pXCJL.1 plasmid to produce the recombinant adenovirus vectors. The promoters used to drive expression of the ribozymes (Rz) are also shown.

FIG. 2 shows cleavage sites for HCV ribozymes Rz1–Rz6 on the HCV RNA plus and minus strands.

FIG. 3 shows the effect of adenovirus-mediated gene transfer of HCV ribozymes into HCV-RNA cell lines. The values represent the mean and standard deviations for five different experiments. Ribozymes 2 and 3 are directed against the negative HCV RNA strand and have no specific effect on plus strand HCV RNA concentrations.

FIGS. 4A and 4B show the Ad.Rz series of ribozyme expression vectors. (4A) depicts the location of ribozyme insertion into the pGvaL plasmid vector. The A/B represent the pol III promoter elements. VaI corresponds to the vaI RNA from human adenovirus. (4B) The pGvaL sequences shown in (A) were cloned into plasmids used to produce recombinant adenovirus vectors. pAd.RzM contains a single, monomeric ribozyme expression cassette while pAd.RzT contains the trimeric expression cassette.

FIGS. 5A–5E show cleavage of plus (5A–5C) and minus (5D–5F) strand HCV RNA expressed from CHO cells. CHO cells that express full length HCV RNAs were infected individually with Ad.RSVRz1-6M or Ad.contr. Three days later RNA was extracted and quantified by in solution hybridization for (5A) plus (5D) minus-strand HCV RNA: (5B, 5E) ribozyme RNA; (5C) neomycin phosphotransferase RNA. The values represent the mean and standard deviation from 3 experiments.

FIG. 6A shows the concentration of human growth hormone serum concentrations in hGH-transgenic mice after ribozyme therapy. Serum samples were analyzed for growth hormone by ELISA analysis at varying times after recombinant adenovirus administration.

FIG. 6B shows hepatic mRNA quantitation in transgenic mice after ribozyme therapy. Ad/RSVhAAT is a control vector; Ad.polIII.Rz is adenovirus containing the hGH ribozyme driven by the adenovirus vaI promoter; Ad.TyRz+ Ad.Ty pol is a 1:1 mixture of the adenovirus expressing nuclear T7 polymerase from the PGK promoter and an adenovirus containing the T7 promoter used to drive transcription of the hGH ribozyme.

FIGS. 7A–7C show the elimination of HCV RNA type 1b from infected hepatocytes. Cultured hepatocytes from an HCV infected individual were infected with a mixture of Ad.Rz1–6M, Ad.RzT 1–6 or Ad.contr. Three days later isolated RNA was quantitated by in solution hybridization for (7A) HCV plus strand RNA; (7B) ribozyme RNA; (7C) hAAT RNA. Values represent the mean and standard deviation from samples analyzed in triplicate.

FIGS. 8A–8C show the elimination of HCV RNA type 1a from infected human hepatocytes. Cultured hepatocytes from HCV infected individual were infected individually with Ad.Rz1–6T or Ad.contr. Three days later isolated RNA was quantitated by in solution hybridization for (8A) HCV plus strand RNA; (8B) ribozyme RNA; (8C) HAAT RNA. Values represent the mean and standard deviation from samples analyzed in triplicate.

DESCRIPTION OF THE SPECIFIC EMBODIMENTS

The present invention provides compositions and methods for treating or preventing hepatitis C infection using therapeutic ribozymes. The ribozymes can be administered in a variety of ways, including by gene therapy targeted to the liver of an individual exposed to or infected by HCV.

A ribozyme of the invention targets the HCV RNA genome and RNA transcripts and copies thereof. Each ribozyme molecule contains a catalytically active segment capable of cleaving the plus or minus strand of HCV RNA, and further comprises flanking sequences having a nucleotide sequence complementary to portions of the HCV RNA. The flanking sequences serve to anneal the ribozyme to the RNA in a site-specific manner. Absolute complementarity of the flanking sequences to the target HCV sequence is not necessary, however, as only an amount of complementarity sufficient to form a duplex with the target RNA and to allow the catalytically active segment of the ribozyme to cleave at the target sites is necessary. Thus, only sufficient complementarity to permit the ribozyme to be hybridizable with the target RNA is required.

As used herein, the term "ribozyme" means an RNA molecule having an enzymatic activity that is able to cleave or splice other separate RNA molecules in a nucleotide base sequence specific manner. By reference to catalytic or enzymatic RNA molecule is meant an RNA molecule which has complementarity in a substrate binding region to a specific HCV RNA plus or minus strand target, and also has enzymatic activity that is active to cleave and/or splice RNA in that target, thereby altering the target molecule. By reference to HCV plus strand is meant one having the same polarity as viral mRNA and containing codon sequences that can be translated into viral protein. The minus strand is a noncoding strand that must be copied by an RNA-dependent polymerase to produce a RNA replicative intermediate.

In preferred embodiments of the present invention the enzymatic RNA molecule is formed in a hammerhead motif but the ribozyme may also be formed in the motif of a hairpin, hepatitis delta virus, group I intron or RNAse P RNA (in association with an RNA guide sequence). Examples of hammerhead motifs are described by Rossi et al., *AIDS Res. Hum. Retrovir.* 8:183 (1992), hairpin motifs are described by Hampel et al., *Biochem.* 28:4929 (1989) and Hampel et al., *Nucl. Acids Res.* 18:299 (1990), the hepatitis delta virus motif is exemplified in Perrotta and Been, *Biochem.* 31:16 (1992), an RNAseP motif is described in Gueerier-Takada et al., *Cell* 35:849 (1983), and examples of the group I intron motif are described in Cech et al., U.S. Pat. No. 4,987,071, each of the foregoing disclosures being incorporated herein by reference. These specific motifs are not limiting in the present invention and those of skill in the art will recognize that an enzymatic RNA molecule of the invention has a specific substrate binding site which is complementary to one or more of the target HCV RNA regions and that it has nucleotide sequences within or surrounding that substrate binding site which impart an RNA cleaving activity to the molecule.

The flanking sequences upstream and downstream of the ribozyme catalytic site may comprise segments of any length that effectively imparts the desired degree of targeting specificity for the ribozyme. Preferably a flanking sequence comprises from about 4 to about 24 nucleotides, more preferably from about 6 to about 15 nucleotides, and typically about 6 to 12, and results in base pairing to the substrate sequence immediately upstream and downstream of the plus or minus strand HCV RNA sequences which comprise the cleavage site.

To select therapeutically useful ribozymes specific for HCV RNA, ribozymes are selected and expressed in whole cells. An optimized expression cassette for the ribozyme can be used where the sequence is embedded in a stable loop region which, in turn, is part of an adenoviral va RNA, so that a catalytic secondary structure can form independently from the surrounding RNA of the expressed RNA. A library of ribozymes flanked by random sequences are cloned into the loop region of the expression cassette. Ribozymes are selected from the library using the HCV RNA target sequence itself. Using this strategy a ribozyme is selected for cleavage sites that are accessible within target HCV RNA and that have structures that permit efficient cleavage. Ribozymes are selected against conserved regions of the HCV genome to be effective against as many HCV strains as possible and to reduce the opportunity for escape variants. The regions include the plus or minus strands of the 5' noncoding region and those coding for the capsid protein and HS5 RNA polymerase. To confirm the effectiveness of the ribozymes in mammalian cells, HCV cDNA is transduced into hepatoma cells to produce intact HCV RNA. Cells which stably produce high level expression of HCV RNA are selected and then transfected with the ribozyme expression cassette. The resulting cleavage of HCV RNA by a ribozyme produces a 5'OH group and a 2'–3' cyclic phosphate group, thereby creating an unstable molecule and decreasing the HCV mRNA concentration within the cell. Ribozyme producing cell lines are compared for the production of HCV RNA and those ribozymes with optimal activity are selected. Cross-reactivity of the ribozyme with different HCV types can also be determined in this system. Ribozymes directed against different target sites in a particular MRNA can be simultaneously isolated using this procedure. This approach has permitted the selection of ribozymes against HCV RNA which completely eliminate HCV RNA expressed in CHO cells.

The site of cleavage in a target HCV RNA molecule is also dependent on the type of ribozyme, e.g., when the ribozyme is of the hammerhead type, the substrate cleavage site is immediately 3' to the sequence NUH, where N is any nucleotide, U is uridine, and H is any nucleotide except G. Different types of ribozymes can be used to achieve the specific cleavage of the targeted HC RNA molecule, e.g., different hammerhead ribozymes (at least 14 different members of this class), the larger Group I introns, RNAse P (which targets tRNA), hairpin ribozymes, hepatitis delta virus ribozyme, etc.

As mentioned above, the HCV RNA target region is typically one that is substantially conserved among the prevalent strains of HCV. These regions include the 5' noncoding region, the capsid protein, and the nonstructural proteins NS-2, NS-3 (helicase), NS-4, NS-5 (RNA polymerase), and conserved regions of E1 (gp30) and NS-1 (gp72), for example. Representative examples of HCV ribozyme target sequences include, for HCV types 1a and 1b (where putative cleave sites are indicated by a "–"), ribozyme 1 (Rz1): GGGAGGTCTCGTAGA [SEQ ID NO: 1] (5' NTR, nucleotides 318 to 332; plus strand), Rz2: GCACCATGAGAGCACGA [SEQ ID NO: 2] (nucleotide 335 to 349; minus strand), Rz3: CCCACAGGACGTCAA [SEQ ID NO: 3] (capsid, nucleotide 395 to 409; minus strand), Rz4: CAACCGTCGCCCACA [SEQ ID NO: 4] (capsid, nucleotide 386 to 400; plus strand), Rz5: TAAAC-CTCAAAGAAA[SEQ ID NO: 5] (capsid, nucleotide 358 to 370; plus strand), and Rz6: GTAAGGTCATCGATA [SEQ ID NO: 6] (capsid, nucleotide 699 to 714; plus strand).

A sequence comprising or encoding said ribozyme or a combination of ribozymes targeted to different portions of the HCV RNA can be delivered in a wide variety of ways to HCV-infected or HCV-susceptible cells to interrupt or prevent HCV infection. The ribozyme can be administered as RNA or expressed from an expression vector. The ribozyme can be administered ex vivo i.e., contacted with cells that have been removed from an infected individual, treated and returned, or the ribozyme can be administered in vivo. Delivery can be via an appropriate delivery vehicle, e.g., a liposome, a controlled release vehicle, by use of iontophoresis, electroporation or ion paired molecules, or covalently attached abducts, and other pharmacologically acceptable methods of delivery. Preferably a carrier provides a means to accumulate the ribozyme at the primary site of HCV infection, i.e., the liver. The ribozyme delivery vehicle can be designed to serve as a slow release reservoir or to deliver its contents directly to the target cell. WO 94/16736 describes a process for evolving RNA molecules to bind receptors on liver cells, to which RNA a ribozyme of the present invention may be tethered for targeting purposes. Alternatively, ribozymes specific for HCV can be attached to ligands or polypeptides which bind to receptors on the target cell. Examples of ribozyme delivery vehicles include liposomes, hydrogels, cyclodextrins, biodegradable nanocapsules, and bioadhesive microspheres. Liposomes can readily be targeted to the liver for delivery of RNA to infected hepatocytes. In a preferred embodiments the anti-HCV ribozyme is administered via an expression vector that is suitable for delivery and expression of an oligonucleotide comprising said ribozyme in a mammalian host cell.

Routes of ribozyme administration include intramuscular, aerosol, intravenous, parenteral, intraperitoneal, etc. The specific delivery route for a selected ribozyme will depend on a variety of factors, such as the form of the ribozyme, the intended target, the stage of disease, etc. For example, while unmodified ribozyme is taken up by cells, modifications can be made to enhance cellular uptake, e.g., by reducing the ribozyme's charge to produce a molecule which is able to diffuse across the cell membrane. The structural requirements necessary to maintain ribozyme catalytic activity are generally recognized in the art, as described in, e.g., Cech. *Curr. Op. Structural Biol.* (1992), which is incorporated herein by reference. Ribozyme modifications to enhance cellular delivery can also be designed to reduce susceptibility to nuclease degradation.

The dosage of ribozyme will also depend on a variety of factors, such as the form of the ribozyme, the route of administration, the severity of infection or stage of disease, the general condition of the patient being treated, and thus can vary widely. Generally the dosage of ribozyme will be between about 10 $\mu$g–200 mg/kg of body weight per day and result in therapeutic or prophylactic levels within the targeted cells sufficient to inhibit or eradicate HCV from the cells. Establishment of therapeutic or prophylactic levels of ribozyme within an HCV-infected cell depends upon, e.g., the rate of uptake (or expression by a particular vector), and rate at which the ribozyme is degraded. The duration of treatment may extend throughout the course of HCV infection or disease symptoms, usually at least about 7–30 days, with longer durations being necessary for severe infections. The number and timing of doses can vary considerably, depending on, e.g., the extent of infection, the efficacy of a particular ribozyme or mixture thereof, the delivery vehicle and route of administration, the judgment of the prescribing physician, etc. As used herein, the terms "treatment" or "treating" refer to any ribozyme-based treatment of HCV or related disease, and include: (1) preventing HCV disease from occurring in a subject who does not have the disease or who has not yet been diagnosed as having it, including prophylactic uses to individuals susceptible to or suspected of exposure to HCV; (2) eradicating, inhibiting or arresting the development of HCV infection or related disease; or (3) regression or reversing the disease.

The ribozymes of the invention may be prepared by chemical synthesis or produced by recombinant vectors according to methods established for the synthesis of RNA molecules. See, e.g., Sambrook et al., *Molecular Cloning, A Laboratory Manual,* 2d ed., Cold Spring Harbor Laboratory Press, Cold Spring Harbor, N.Y. (1989), incorporated herein by reference. The ribozyme sequence may be synthesized, for example, using RNA polymerases such as T7 or SP6. The ribozymes of the invention may be prepared from a corresponding DNA sequence (DNA which on transcription yields a ribozyme) operably linked to an RNA polymerase promoter such as the promoter for T7 RNA polymerase or SP6 RNA polymerase. A DNA sequence corresponding to a ribozyme of the present invention may be ligated in to a DNA vector, such as a plasmid, bacteriophage or other virus. Where the transfer vector contains an RNA polymerase promoter operably linked to DNA corresponding to a ribozyme, the ribozyme may be conveniently produced upon incubation with an RNA polymerase. Ribozymes may therefore be produced in vitro by incubation of RNA polymerase with an RNA polymerase promoter operably linked to DNA corresponding to a ribozyme, in the presence of ribonucleotides. In vivo, procaryotic or eucaryotic cells (including mammalian cells) may be transfected with an appropriate vector containing genetic material corresponding to a ribozyme in accordance with the present invention, operably linked to an RNA polymerase promoter such that the ribozyme is transcribed in the host cell. Ribozymes may be directly transcribed in vivo from a transfer vector, or alternatively, may be transcribed as part of a larger RNA molecule. For example, DNA corresponding to ribozyme sequence may be ligated into the 3' end of a carrier gene, for example, after a translation stop signal. Larger RNA molecules may help to stabilize the ribozyme molecules against nuclease digestion within the cells. On translation the carrier gene may give rise to a protein, whose presence can be directly assayed if desired, for example, by enzymatic reaction when the carrier gene encodes an enzyme.

In one exemplary method of producing a ribozyme, two synthetic oligonucleotides of complementary sequence are prepared by standard procedures on an automated DNA synthesizer and hybridized together, where one of the oligonucleotides encodes a desired ribozyme. The respective ends of the hybridized oligonucleotides correspond to different restriction enzyme sites and, after appropriate cleavage, the double stranded DNA fragment is cloned into a transfer vector. Where the plasmid vector contains a RNA polymerase promoter upstream from the DNA sequence corresponding to a ribozyme of the present invention, RNA transcripts corresponding to the ribozyme are conveniently prepared either in vitro or in vivo. When in vivo, that is, within the cell or cells of an organism, a transfer vector such as a bacterial plasmid or viral RNA or DNA encoding one or more ribozymes may replicate and/or be transcribed by cellular polymerases to produce ribozyme RNAs which can then inactivate a desired target HCV RNA sequence. The transfer vector may become integrated into the genome of the host cell and transcription of the integrated genetic material gives rise to ribozymes which act to inactivate the target HCV RNA.

Accordingly, a viral vector containing a sequence corresponding to a ribozyme of the present invention can be prepared in any of a wide variety of ways. Representative retroviral vectors suitable for use in the present invention are described, for example, in U.S. Pat. Nos. 4,861,719, 5,124, 263 and 5,219,740, Kay et al., *Hum. Gene. Ther.* 3:641–647 (1992) and Kay et al., *Science* 262:117–119 (1993), each of which is incorporated herein by reference. Other vectors may also be employed, particularly for the ex vivo methods described herein, such as DNA vectors, pseudotype retroviral vectors, adenovirus, adeno-associated virus, gibbon ape leukemia vector, VSV-G (e.g., as described in WO 94/29440), VL30 vectors, liposome mediated vectors, and the like.

Because adenovirus is capable of infecting dividing and non-dividing hepatocytes at high efficiency, in a preferred embodiment the vector is an adenovirus including, for example, adeno-associated viral vectors. Representative adenoviral vectors which can be used to encode the ribozymes of the present invention are described in Stratford-Perricaudet et al., *J. Clin. Invest.* 90:626–630 (1992), Graham and Prevec, in Methods in Molecular Biology: Gene Transfer and Expression Protocols, 7:109–128 (1991) and Barr et al., *Gene Therapy,* 2:151–155 (1995), WO 94/20146, WO 94/26915, and WO 94/29471, and adeno-associated vectors are described in U.S. Pat. No. 5,436,146, each of which is incorporated herein by reference. A preferred adenovirus plasmid for producing recombinant adenovirus which drives transcription of a ribozyme of the invention is the pXCJL.1 plasmid described in Spessot et al., *Virology* 168:378–387 (1989), incorporated herein by reference. An adenoviral vector may include essentially the complete adenoviral genome (Shenk et al., *Curr. Top. Microbiol. Immunol.* 111:1–39 (1984) or may be a modified adenoviral vector in which at least a portion of the adenoviral genome has been deleted. In a preferred embodiment, the adenoviral vector comprises an adenoviral 5' LTR, an adenoviral 3' ITR, an adenoviral encapsidation signal; at least one DNA sequence encoding a ribozyme of the present invention; and a promoter controlling the transcription of the ribozyme or an RNA polymerase and a promoter controlling the transcription of the RNA polymerase sequence, e.g., T7 polymerase controlled by the PGK promoter. The vector is typically free of at least the majority of adenoviral E1, E2 and E4 DNA sequences.

The vector is preferably packaged into infectious nonreplicating, recombinant adenoviral particles using, e.g., a helper adenovirus or cell line which provides the necessary encapsidation materials. Preferably the helper virus has a defective encapsidation signal so the helper virus will not encapsidate itself. An example of an encapsidation defective helper virus which may be employed is described in Grable et al., *J. Virol.* 66:723–731 (1992), incorporated herein by reference.

The vector and the encapsidation defective helper virus are transfected into an appropriate cell line for the generation of infectious viral particles. Transfection may take place by electroporation, calcium phosphate precipitation, microinjection, or through proteoliposomes. Examples of appropriate cell lines include, but are not limited to HeLa cells or 293 (embryonic kidney epithelial) cells (ATCC No. CRL 1573). The infectious viral particles (i.e., the adenoviral vector) may then be transduced into eucaryotic cells, such as hepatocytes, whereby the DNA sequence encoding a ribozyme is expressed by the eucaryotic cells in a host.

The viral vector, consisting of infectious, but replication-defective, viral particles, which contain at least one DNA sequence encoding a ribozyme effective against HCV RNA, is administered in an amount effective to inhibit or prevent HCV infection in a host. The vector particles may be administered in an amount from 1 plaque forming unit to about $10^{14}$ plaque forming units, more preferably from about $1 \times 10^6$ plaque forming units to about $1 \times 10^{13}$ plaque forming units. A sufficient number of adenoviral vector particles containing a sequence corresponding to a ribozyme of the invention should be administered to the liver to infect up to at least about 50% of the hepatocytes, usually about 80%, preferably about 95%, and more preferably 99% to 99.99% or more of the hepatocytes in the individual, e.g., typically from about 10 up to about 100 or more adenovirus particles per hepatocyte are administered. The host may be a human or non-human animal host. A preferred non-human animal host is a mammal, more preferably a non-human primate or a non-human mammal having a liver which is comprised at least partially of human hepatocytes, as more fully described herein. The adenovirus vector can be administered by a variety of routes, but typically systemically, such as, for example, by intravenous administration (e.g., peripheral vein injection), by infusion via the portal vein, to the bile duct, intramuscularly, intraperitoneally, or intranasally.

The expression of the ribozyme sequence encoded by the vector can be constitutive or inducible, but preferably is constitutive. As the hepatocytes which express the ribozyme inhibit the proliferation of and are capable of eradicating HCV, virus-free hepatocytes may repopulate the liver. Thus, over a period of days to weeks hepatocytes treated with the anti-HCV ribozyme may repopulate the liver. The entire treatment process itself may be repeated as necessary, understanding that a humoral immune response to certain vectors, e.g., adenovirus vector, may be generated by repeated administration. The immune response may alleviate the effect of vector administration and thus necessitate administration of larger quantities of the vector, administration of a different vector to which the patient is not immune, delivery of the vector in a manner by which the particles are shielded from the host's immune system, or tolerization of the host's immune system to the vector.

The vector encoding the anti-HCV ribozyme is also used to transduce hepatocytes which have been isolated from a patient. In some cases, e.g., extreme hepatocellular disease, it may be desirable to use hepatocytes which have been isolated from a suitable uninfected donor, i.e., one who is substantially the same or closely related in histocompatibility type, as may be the case for a liver transplant. The transduced hepatocytes may be cultured for up to 5 to 10 days or longer before being administered to the patient, but typically the cells will be administered by infusion, typically via the portal or splenic vein, in single or multiple administrations, within 1–5 days after removal. For ex vivo transduction the viral vector is preferably a retroviral vector, although other vectors may also be used. In the case of liver transplants, the liver may be transduced with the vector, e.g., adenovirus, prophylactically prior to transplant, while in the donor or ex vivo, or after transplant but before HCV infection of the donor liver is substantially established.

The invention provides a method of inhibiting hepatitis C virus RNA replication or expression wherein two or more different ribozymes specific for hepatitis C virus RNA are introduced into a cell infected with hepatitis C virus. Although use of a single ribozyme will suffice to treat or reduce the severity of HCV infection, the use of two or more different ribozymes offers therapeutic advantages because it ensures that a more complete destruction of the RNA is achieved. Similarly, with multiple ribozymes there is less possibility for a resistant species to survive and escape therapy. Therefore, a combination of ribozymes against different regions of the RNA essentially ensures recognition of all the major viral genotypes and cleavage in at least one location of the RNA genome.

As with the use of a single ribozyme for treating or reducing the severity of hepatitis C viral infection, the use of multiple ribozymes are similarly selected to target conserved or functional regions of the HCV RNA. For example, the 5' end of the viral genome can be targeted to eliminate translation of the polyprotein and each of the individual viral proteins. Selection of ribozymes against the capsid and other conserved region of the hepatitis C RNA will also be effective in destroying the function of the HCV RNA. Alternatively, cleavage of the minus strand will abolish the replication of full length plus strands of the viral RNA. This cleavage can also lead to the inhibition of RNA packaging and translation of truncated plus strands. Thus, by judicially selecting the region and strand of the HCV RNA to target, a more efficacious result can be achieved. For example, the simultaneous elimination of both strands can be achieved by using two or more different ribozymes which are selected against opposite strands of the HCV RNA. This simultaneous elimination of both strands offers the additional advantage in that both replication and transcription of hepatitis C RNA can be inhibited leading to synergistic effects in decreasing viral load.

The introduction of two or more ribozymes into a cell infected with HCV can be accomplished by, for example, any of the methods described previously as well as others known to those skilled in the art. Thus, multiple ribozymes can be introduced into an infected cell using, for example, any of the previously described ribozyme delivery vehicles as either synthetic or recombinantly produced RNA molecules. Alternatively, the ribozyme delivery vehicle can be an expression vector or viral vector encoding two or more different ribozymes which can be expressed following introduction into the infected cell. A specific example of the introduction and expression of two or more ribozymes is described below in Example IV. Thus, the invention also provides compositions for inhibiting hepatitis C virus RNA replication or expression. The compositions include two or more different ribozymes which are specific for the hepatitis C virus RNA.

The invention also provides non-human mammals with functional non-native liver, e.g., human, or native liver which expresses a desired gene product. The animals can be used as models for evaluating a wide variety of disease processes and treatments. For example, the animal models can be used to as models of pathogenesis for infections, e.g., viral infections such as hepatitis C or the like, or to determine the effectiveness and safety of treatments described herein for such infections.

In one embodiment the non-human animals of the present invention contain a transgene which encodes a modified non-secreted uPA as described herein, e.g., uPA having a modified C-terminus containing KDEL, uPA having the signal peptide on the N-terminus substituted by the RR retention signal and transmembrane region of the type II transmembrane proteins (Schutze et al., *EMBO J.* 13:1696–1705 (1994); Gorlich et al., *Nature* 357:47–52 (1992), or a combination of both C-terminal and N-terminal modifications designed to inhibit secretion of the uPA molecule without substantially adversely affecting hepatotoxic activity. Expression of the modified uPA can be under the control of an inducible or constitutive promoter, e.g., the cytochrome P450 promoter of Jones et al., *Nucl. Acids Res.* Simultaneous with or subsequent to expression of the secretion-impaired uPA transgene, non-native (e.g., human) hepatocytes are implanted in the transgenic mammal, e.g., a nude or immunodeficient scid mice, to reconstitute the mammal's liver with a large proportion of non-native (e.g., human) hepatocytes. The mammal is then used as a model for human hepatitis C infection and its treatment, e.g., with ribozymes against HCV RNA as described herein.

In another embodiment the mammal can be transduced with an adenoviral vector encoding the modified, secretion-impaired uPA or a hepatotoxin which inhibits or kills hepatocytes, and the non-native cells implanted. The mammal's liver is reconstituted with the non-native hepatocytes and the animal used as described above. Typically the hepatotoxin is one such as uPA, or tPA can be used to stimulate hepatocyte regeneration de novo without causing liver damage. The molecule which stimulates hepatocyte regeneration, with or without hepatotoxic activity, should be specific for hepatocytes, or if not specific, should not be secreted by the infected hepatocytes into the bloodstream. A representative example is uPA which has been modified by N-terminal and/or C-terminal modifications as described herein so as to inhibit secretion by the infected host cell. In some cases other toxins may be used, where they are placed under the control of tissue-specific (liver) promoters and are not secreted, or the vectors are specifically targeted to hepatic tissue. These toxins include the cytotoxic domain of bacterial toxins such as Pseudomonas exotoxin A, diphtheria toxin, cholera toxin, shiga and shiga-like toxin, ribosome inactivating toxins derived from plants and fungi (e.g., ricin), hepatocyte growth factor, and others described in *Genetically Engineered Toxins*, ed. A. Frankel, Marcel Dekker, Inc. 91992), incorporated by reference herein.

In the animal model, the sequences encoding the selected ribozymes are placed into adenoviral vectors and used to transduce the hepatocytes of the animal of interest, e.g., mice in which the liver has been ablated with the urokinase gene as described herein and reconstituted with human hepatocytes. For example scid mice that have livers reconstituted with human hepatocytes are infused with hepatitis C particles, or human HCV-infected hepatocytes are used in the reconstitution process. The liver and serum of the animals are monitored for production of virus by quantitative RT-PCR assays. Additionally, immunohistochemical staining of tissues or antigen detection in the blood can be performed. The ribozyme-expressing adenovirus is delivered to the animal and efficacy of HCV inhibition observed.

It is understood that modifications which do not substantially affect the activity of the various embodiments of this invention are also included within the definition of the invention provided herein. Accordingly, the following examples are intended to illustrate but not limit the present invention.

EXAMPLE I

This Example describes the construction of an expression unit for a ribozyme library so as to achieve a high level of expression and stability of the expressed ribozyme and the identification of specific ribozymes for HCV.

Construction and function of the expression cassette

To construct the ribozyme expression vector, oligonucleotides were synthesized in an automatic synthesizer (Applied Biosystems). The genes for vaRNAs I and II were cloned as an XbaI-NsiI fragment (Akusjarvi et al., *Proc. Natl. Acad. Sci. USA* 77:2424–2428 (1980) in the XbaI-PstI site of pGEM7zf+ after prior deletion of the AatII site in pGEM. The resulting plasmid was named pGva. Oligonucleotides I 5'CGTCGACTGCTGCAGTGCAGCGTGTG-GACCCAACGACACGCGGGCGGTAACCGAC GT3' [SEQ ID NO: 7] and II 5'CGGTTACCGCCCGCGT-GTCGTTGGGTCCACACGCTGCACTGCAG-CAGTCGACGAC GT3' [SEQ ID NO: 8], (10 ng each), which represent both strands of the sequence to form a loop, were annealed in 20 mM Tris-HCl (pH 7.5)-10 mM $MgCl_2$ by heating for 5 min. at 85° C. and slow cooling to room temperature and cloned into the AatII site within the va gene sequence. The resulting plasmid was designated pGvaL. The 5' end of oligonucleotides III 5'CCGCTCGAG(N)$_{13}$CTGATGAGTCCGTGAGGACGAAA3' [SEQ ID NO: 9] and IV 5'TGCATGCAT(N)$_{11}$N$_G$TTTCGTCCTCACGGACTCATCAG3' [SEQ ID NO: 10] where N$_G$ is 40% C, 40% G, 10% T, and 10% A, for the randomly mutated ribozymes were phosphorylated with polynucleotide kinase.

Oligonucleotides III and IV (5 µg each) were heated for 5 min. at 85° C. in 20 mM Tris-HCl (pH 7.5)-10 mM MgCl$_2$ cooled to 65° C., and incubated with 200 µM deoxynucleoside triphosphates-(dNTPs) 2.5 U of Taq polymerase for 30 min at 65° C. After phenol extraction and ethanol precipitation, the double-stranded oligonucleotides were digested with NsiI-XhoI overnight and cloned into the SalI and PstI sites of pGvaL. Ligation products were transformed in highly competent ($10^{10}$ colonies per µg of DNA) E. coli DH5, and plasmid DNA from a pool of $10^{10}$ different individual clones was prepared. The ribozyme gene library was designated GvalRz. The corresponding RNAs were designed va, vaL and ValRz.

T7 polymerase-dependent in vitro transcription was performed by incubating 2 µg of DNA template, 12.5 µl of TKB (20 mM Tris-Hcl [pH 7.9], 0.2 mM EDTA, 10 mM 2-mercaptoethanol, 0.1 M KCl, 20% glycerol, 0.5 mM phenylmethysulfonyl fluoride, 10 mM MgCl$_2$), 10 U of RNasin, 2.5 µl of 5 mM NTPs (or 5 mM ATP, GTP, and TTP plus 20 µCi of [$^{32}$P]CTP and 1 mM CTP), 5 mM MgCl$_2$, 2.5 µl of 10 mM dithiothreitol, 100 U of T7 RNA polymerase (Biolabs) in a total volume of 25 µl at 37° C. for 60 min. After digestion with 23 U of DNase I, the transcripts were purified twice by phenol extraction and ethanol precipitated. The amount of RNA synthesized was estimated after gel electrophoresis in an ethidium bromide-stained agarose gel calibrated with concentration markers. In a standard reaction, 5 to 8 µg of RNA per 25-µl reaction volume was synthesized.

Function and stability of the chimeric ribozyme RNA.

Cleavage reactions with ribozymes were performed in vitro. For analytical analysis, 100 nM ribozyme and 100 nM in vitro-transcribed substrate human growth hormone (hGH) RNA or HCV plus RNA (type 1α) were mixed in a 15-µl reaction volume containing 50 mM Tris (pH 7.5) and 1 mM EDTA. For heat denaturation, the mixture was boiled at 95° C. for 90 s and quickly cooled on ice. MgCl$_2$ (10 mM) was added, and the mixture was incubated at 37° C. for 30 or 60 min. The reaction was stopped by addition of an equal volume of stop solution (95% formamide, 20 mM EDTA, 0.05% bromphenol blue, 0.05% xylene cyanol), the mixture was heated at 95° C. for 2 min., and the products were analyzed in a 4 or 6% polyacrylamide-8M urea gel in Tris-borate EDTA buffer.

Total-cell RNA was extracted by the guanidinium-phenol method (Chomczynski and Sacchi, *Anal. Biochem.* 162:156–159 (1987)) or with the RNaid Plus Kit (Bio 101, La Jolla, Calif.). Total hGH-RNA was extracted from a hGH expressing cell line. Total HCV (type 1b)-RNA was extracted from HCV positive human liver.

For northern blot analysis, RNA samples were fractionated on a 1.5% agarose gel containing 2.2 M formamide and transfected by Hybond N+ nylon membrane. Northern (RNA) hybridization was carried out with $^{32}$:-labeled probes by the method described by Westneat et al., *Nucl. Acids Res.* 16:4161–4170 (1988)). HCV and vaDNA sequences were labeled by standard random-priming techniques with DNA pol I (Klenow fragment).

Creation of a functional ribozyme library.

Cleavage of cellular RNA in vitro ribozymes from the library. Purified total-cell RNA was used as the source of mRNA.

Cleavage was carried out at the physiological pH (50 mM Tris-HCl [pH 7.5]) at 37° C. for 1 hour in a 15-µl reaction volume with or without prior heat denaturation (for 90 s at 95° C.). The cleavage products were analyzed in a 2% ethidium bromide-stained NuSieve agarose gel and could be detected as a smear between the 18S and 28S rRNAs and below the 18S rRNA. In some cases, the 5'-OH groups of cleavage products were phosphorylated with [$^{32}$p]ATP by using polynucleotide kinase and quantified on a Fuji Phosphorimager after polyacrylamide gel electrophoresis.

For the cleavage reaction purified total RNA (1 µg per reaction) and 10 µg of vaL (as control) or vaLRz (library) RNA, which were synthesized by T7 polymerase, were mixed and incubated in 50 mM Tris-HCl-10 mM MgCl$_2$ for 1 h at 37° C. with or without prior heat denaturation. No significant self-digestion of ribozymes was observed. The ribozyme cleavage was three times more efficient when the reaction mixture was heat denatured. Without addition of 10 mM MgCl$_2$, no specific cleavage reaction was detected. For further analyses, cleavage products were used without prior heat denaturation.

After the reaction, RNA was purified with oligo(dT)-cellulose (PolyATract mRNA Isolation System; Promega) according to the manufacturer's specifications. After purification, 0.05 to 0.5 µg of RNA was annealed with 2.5 µM oligo(dT) primer (Promega) for 10 min. at 70° C., and unbound primer was separated by centrifugation through a 30,000-molecular-weight-cutoff filter unit (Millipore). Reverse transcription was performed with 200 U of superscript II reverse transcriptase (Bethesda Research Laboratories) at 37° C. for 1 h. To eliminate free primers, cDNA-RNA hybrids were purified with Gene Clean (Bio 101). The cDNA-RNA hybrid in 30 µl of H$_2$O was boiled for 2 min. and cooled on ice. Tailing was carried out for 15 min. 37° C. in a total volume of 50 µl containing 200 µM dGTP, 20 U of terminal deoxynucleotidyltransferase (Bethesda Research Laboratories), and tailing buffer.

A 5% portion of the tailing-reaction mixture was used for the first PCR with 200 µM dNTP, 1.5 mM MgCl$_2$, and 2.5 U of Taq polymerase in buffer containing 2% dimethyl sulfoxide, 50 mM KCl, 10 mM Tris-HCl (pH 7.9), and 0.1% Triton X-100 in a 100-µl reaction volume. The initial seven cycles (30 s at 95° C., 30 s at 42° C., and 90 s at 72° C.) were run in the presence of 15 µm C-Primer (5'GAGAATTCTAGAGGATCCCCCCCCCCCC3' [SEQ ID NO: 11]) only. After addition of 250 µM hGH-specific primer (5'GAGAATTCCAAGGCCAGGAGAGGCACTGGGGA3' [SEQ ID NO: 12]), which is specific for a region immediately upstream of the poly(A) signal of the genomic hGH gene. PCR-primers for selecting HCV ribozymes are directed against sequences in the 5' untranslated region and capsid region of the HCV genome (see FIG. 2), and comprised: C1+: 5'GTAAACTCCACCAACGATCT [SEQ ID NO: 13]; C2+5'GAAGATAGAGAAAGAGCA [SEQ ID NO: 14]; C3+: 5'ACCCCATGAGGTCGGCGAA [SEQ ID NO: 15]; C1-: 5'CTGTGAGGAACTACTGT [SEQ ID NO: 16]; and C2-: 5'CACGCAGAAAGCGTCTAGCC [SEQ ID NO: 17]. PCR was done for 40 cycles (60 s at 94° C. and 90 s at 72° C. or 60 s at 95° C., 45 s at 65° C., and 60 s at 72° C.). The reaction mixture was run on a native 5% PAA gel in Tris-acetate buffer. HCV specific bands were identified by Southern blot with a $^{32}$P-labeled 730 bp fragment (XbaI/

ClaI) of pTET/HCV5'T7G3'AFL (Lemm, Kolyakhov, Heise, Feinstone and Rice). Specific bands were cut out and purified with Gene Clean. The resulting fragments were cloned in the PGEM-T II vector system (Promega). Clones corresponding to the 5' end of individual RNA downstream cleavage products were sequenced with the fmole sequence kit (Promega).

Identification of specific ribozymes in the library.

Amplification of ribozymes. Ribozyme genes from the library were amplified as follows. PCR was performed by incubating 50 ng of plasmids from the ribozyme library, 20 µM each upstream and downstream primer (which are specific for the sequences around the GTC/CTC site and 2.5 U of Taq polymerase in buffer containing 2% dimethyl sulfoxide, 50 mM KCl, 10 mM Tris-HCl (pH 7.9), and 0.1% Triton X-100 in a 100-µl reaction volume for 40 cycles (45 s at 95° C., 45 s at 52° C., and 45s at 72° C.). Specific fragments were prepared as described above, digested with XhoI-NsiI, cloned into the SalI and PstI sites of GvaL, and sequenced with the T7 promoter primer.

Cell culture. Cells were grown in Dulbecco's modified Eagle's medium containing 200 mM asparagine, 200 mM proline, 200 mM glutamine, and 10% fetal calf serum (GIBCO, Grand Island, N.Y.) under a 5% $CO_2$ atmosphere.

Transfection. Plasmids were purified by two rounds of cesium chloride gradient centrifugation. For transfection of CHO cells, a modification of the standard calcium phosphate coprecipitation method was used (Lieber et al., *Nucl. Acids Res.* 17:8485–8493 (1989)). DNA (10 µg) in 220 µl of $H_2O$ was mixed with 30 µl of 2 M $CaCl_2$ and 250 µl of 2× HBS (50 mM HEPES, 280 mM NaCl, 1.5 mM sodium phosphate [equal amounts of mono- and dibasic] [pH 6.96] was added dropwise while the mixture was vortexed. The precipitate was added to 5 mL of culture medium in 25-cm² tissue culture flasks containing 2.5×10⁵ CHD cells that had been seeded the day before. Cells were transfected with a mixture of 8 µg of pTET HCV (Lemm et al., supra) test plasmid, and 1 µg of pSV2neo (Southern and Berg, *J. Mol. Appl. Genet.* 1:327–341 (1982)). After 48 h, 1/10 of the cells were subjected to selection with 600 µg of G418 per ml to generate pools of about 100 colonies in order to test for stable expression levels. The cell line was named HCV-CHO.

Among 25 HCV RNA specific amplification products detected using the methods described above, thirteen (nine for plus RNA, four for minus RNA) were identified as downstream ribozyme cleavage products following a GUC or CUC ribozyme recognition site. Of these thirteen HCV specific ribozymes, attention was directed to six potential cleavage sites based on the following criteria: (1) localization near the AUG, such that most of the untranslated region is deleted and/or the IRES secondary structure is disrupted; (2) flanking regions and cleavage sites for ribozymes contained within highly conserved regions for HCV types 1a and 1b; and (3) localization within single-stranded or loop regions in a secondary structure model of HCV RNA.

To confirm activity and to map the cleavage site, ribozyme genes with about 7 or 8 flanking nucleotide regions were cloned into the pGvaL expression cassette described above. The ribozymes were embedded into the stem loop structure which is part of an adenoviral vaI RNA with an internal pol III promoter such that the catalytic sequences could be formed independently from surrounding RNA structures. Ribozymes expressed from this vector were assayed for activity as described below.

In vitro RNA transcription products obtained from ribozyme genes cloned into GvaL were incubated with a radiolabeled, 730 nt long HCV 1a (plus strand) RNA generated by T7 polymerase in vitro transcription. For all ribozymes, in vitro cleavage products of expected size were obtained.

Figure 2:
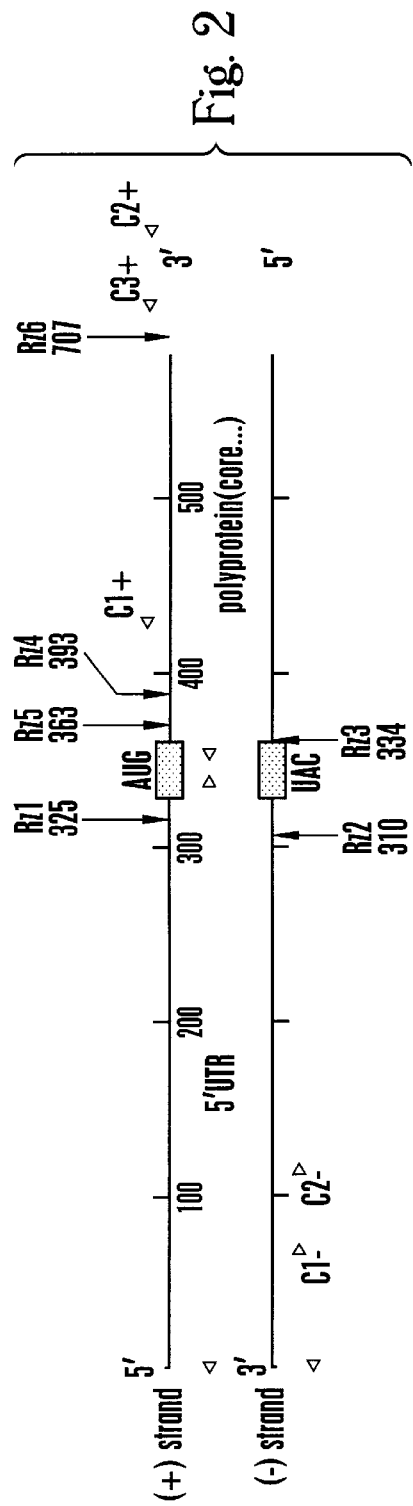

FIG. 2 shows cleavage sites for these six HCV ribozymes, designated Rz1–Rz6, on the HCV RNA plus and minus strands. The HCV ribozyme target sequences are as follows, based on a CDNA sequence that corresponds to the HCV type 1a and type 1b RNA, where the putative ribozyme cleavage sites are indicated by a "–": ribozyme 1 (Rz1): GGGAGGTCTCGTAGA [SEQ ID NO: 1] (5' NTR, nucleotides 318 to 332; plus strand), Rz2: GCACCATGAG-CACGA [SEQ ID NO: 2] (nucleotide 335 to 349; minus strand), Rz3: CCCACAGGAGTCAA [SEQ ID NO: 3] (capsid, nucleotide 395 to 409; minus strand), Rz4: CAAC-CGTCGCCCACA [SEQ ID NO: 4] (capsid, nucleotide 386 to 400; plus strand), Rz5: TAAACCTCAAAGAAA [SEQ ID NO: 3] (capsid, nucleotide 358 to 370; plus strand), and Rz6: GTAAGGTCATCGATA [SEQ ID NO: 6] (capsid, nucleotide 699 to 714; plus strand). In summary, the four ribozymes designated Rz 1, 4, 5, 6 cleaved the HCV plus RNA at positions 325, 393, 363, 707, respectively and ribozymes designated Rz 2 and 3 cleaved the minus strand at positions 342 and 401, respectively.

EXAMPLE II

Ribozyme-Mediated Inhibition of HCV RNA

This Example shows the inhibition of HCV RNA expression following adenovirus-mediated gene transfer and expression HCV-specific ribozymes in HCV expressing cell lines.

Figure 3:
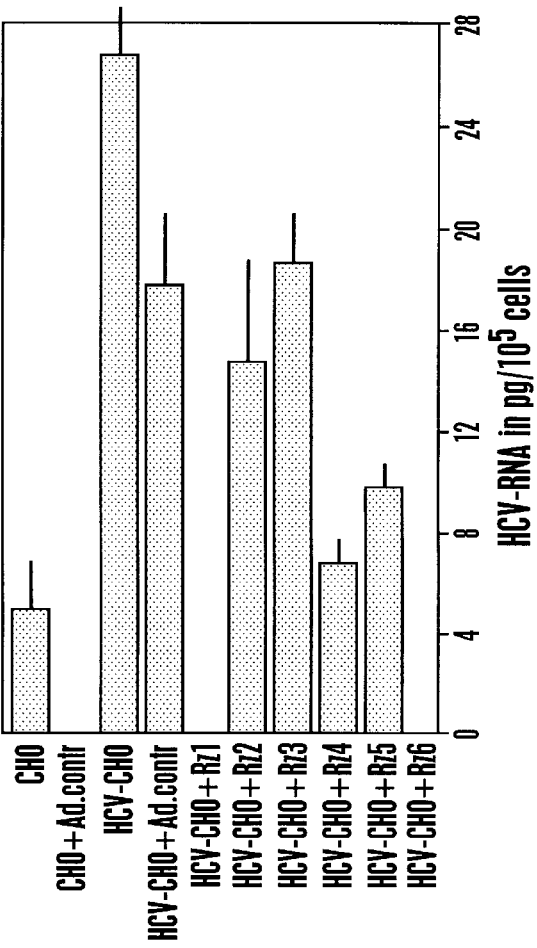

Sequences encoding the HCV-specific ribozymes were cloned into the pXCJL.1 plasmid (Spessot et al., *Virology* 168:378–387 (1989)) to produce recombinant adenovirus vectors. The effect of adenovirus-mediated gene transfer of the HCV ribozymes on HCV RNA in an HCV-RNA expressing cell line was then determined. 1×10⁶ CHO cells that express about 40–60 copies of plus strand HCV RNA per cell were incubated for 4 hours with 1000 pfu/cell of recombinant adenovirus vectors (the amount of virus that transduces 100% of CHO cells) that express ribozymes 1 through 6 or an irrelevant control vector. Forty hours later, total nucleic acid was extracted from harvested cells and HCV specific RNA was quantified by solution hybridization with an oligonucleotide specific for HCV type 1a (nt 324–352) within the 5' NCR. The results are shown in FIG. 3, where the values represent the mean and standard deviations for five different experiments. A minor non-specific HCV signal was seen in normal CHO cells, and transduction with an irrelevant control resulted in a minor reduction in HCV RNA signal. Ribozymes 2 and 3 are directed against the negative HCV RNA strand and had no specific effect on plus strand HCV RNA concentrations.

In order to better characterize the above selected HCV ribozymes, their activity was further quantitated following adenoviral gene transfer in vivo. For these studies, CHO cells which stably express either the HCV (1a) plus strand as described above (CHO (+)HCV) or the HCV (1a) minus strand (CHO (–)HCV) hepatitis C viral RNA under the transcriptional control of the T7 promoter were generated. These vectors are derivatives of the pGvaL (see Example I and FIG. 4A) and the pXCJL.1 vectors (see above and FIG. 1) described previously. Briefly, the ribozymes were cloned into recombinant adenovirus vectors because these vectors can transduce virtually all hepatocytes with at least 15–30 genome copies per cell in animals (Vrancken Peeters et al.,

*Biotechniques* 20:278–285 (1996)). The ribozyme genes were placed under control of the RSV-LTR promoter in one or three copies (FIG. 4B). The ribozymes contained as three copies can be transcribed from the pol II promoter either as one RNA containing three ribozymes or as three single RNAs from the internal pol III promoter (see FIG. 4B). Cell lines expressing these Ad.Rz vectors produced approximately 45–60 HCV genomes/cell.

Briefly, CHO cell lines were constructed to express either the positive or negative HCV RNA as follows. For the CHO cell line expressing the positive strand, a HCV type 1a (9.4 kb) CHO-(+) RNA was used. This RNA was under the control of a T7 phage promoter the plasmid pTET/HCV5'TyG3'AFL (J. A. Lemm, M. Heise, and C. M. Rice, unpublished) and was cotransfected with pSV2neo (ratio 20:1) into CHO cells. Stable colonies were selected with 600 µg/ml G418. The T7 promoter drives expression as a pol II promoter (Lieber et al., *Eur. J. Biochem.* 217:387–394 (1993). Approximately 100 colonies were pooled and analyzed for HCV-RNA expression by in solution hybridization.

To express the minus strand of the HCV RNA, an initial plasmid (pGasHCV) was generated by cloning the HCV genome in antisense orientation behind a T7 promoter in pGEM2. However, in order to delete the T7 promoter from the 5' end of pTET/HCV (+) a 579 bp fragment of the HCV 5' end was amplified by PCR with the following primers: 5'-CGTCTAGAGCCAGCCCCCTGATGGGG (SEQ ID NO:18) and 5'-AAGGGTACCCGGGCTGAGC (SEQ ID NO:19). The 579 bp KpnI/XbaI PCR fragment and the 7625 bp EcoRI/KpnI fragment from pTET/HCV+ were cloned into the EcoRI/XbaI sites of pGEM2. CHO cells stably expressing HCV minus RNA (CHO-(-) HCV) were generated as described for CHO—(+) HCV.

In solution hybridization was used to quantitate HCV RNA following ribozyme expression. Briefly, 10 µl total RNA (20 µg) was mixed with 20 µl oligo-salt mix containing 6 vol $H_2O$, 3 vol 10× hybridization salts (3M NaCl, 100 mM Tris-HCl, pH 7.5, 20 mM EDTA) and 1 vol oligonucleotide (10,000–15,000 cpm) and incubated overnight at 45° C. in an Ericomp thermocycler with cover heating. After hybridization samples were diluted with 1 ml S1 nuclease buffer (1 vol 10× S1 buffer: 3M NaCl, 0.3 M sodium acetate, 0.03 M Zinc acetate, pH 4.5, 1 vol herring sperm DNA (1 mg/ml), 8 vol $H_2O$), and incubated for 1 hour at 37° C. with 8 to 24 units of S1 nuclease (Gibco). The S1 resistant nucleic acids were precipitated with 100 µl 6 M trichloroacetic acid (TCA) for 1 hour on ice, then collected on glass filters (Whatman GF/C), and washed 3 times with cold 3% TCA, 1% NaPPi and once with 95% ethanol before being counted in a scintillation cocktail for 5 minutes on a Packard scintillation counter.

The S1 nuclease concentration was optimized for each oligonucleotide used for hybridization according to the procedure described in Durnam and Palmiter (Durnham and Palmiter *Anal. Biochem.* 131:385–393 (1983)). Each set of hybridizations included a standard curve with quantified amounts of a corresponding in vitro transcribed RNA (1–150 pg/reaction). The oligonucleotides used for in solution hybridization were: HCV(+)RNA: nt 409 5'-TGACGTCCTGTGGGCGACGGTTGGTG (SEQ ID NO:20); HCV(-)RNA: nt 251 5'-AGCCGAGTAGTGTTGGGTCGCGAAAGG (SEQ ID NO:21), neomycin phosphotransferase RNA: nt 42 5'-AGCGGCCGGAGAACCTGCGTGCAATC (SEQ ID NO:22); ribozyme RNA: 5'-TCGTTGGGTCCACACGCTGCACTGCAT (SEQ ID NO:23) (against the cloned loop). Hybridization was for 18 hours at 45° C. For hAAT RNA: nt 157 5'-TGTTGAAGGTTGGGTGATCCTGATCATGG (SEQ ID NO:24) was mixed with RNA preheated for 5 minutes at 85° C. and then hybridized for 30 hours at 55° C. Standard RNAs were generated by T7 polymerase in vitro transcription.

To analyze the activity of the above described ribozymes, the Ad.Rz vectors were infected onto confluent HCV (+) CHO cells or HCV (-) CHO cells (at an moi sufficient to transduce 100% of cells), and 3 days post infection total cell RNA was analyzed for HCV RNA, ribozyme RNA and neomycin phosphotransferase (control) RNA concentrations by quantitative in solution hybridization (FIG. 5).

Figure 5A:
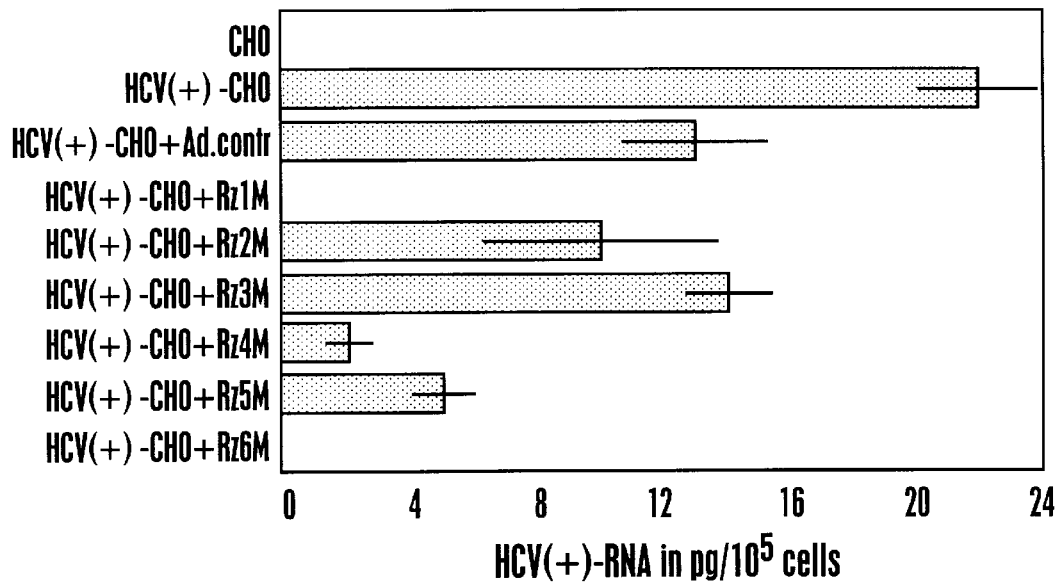
Figure 5B:
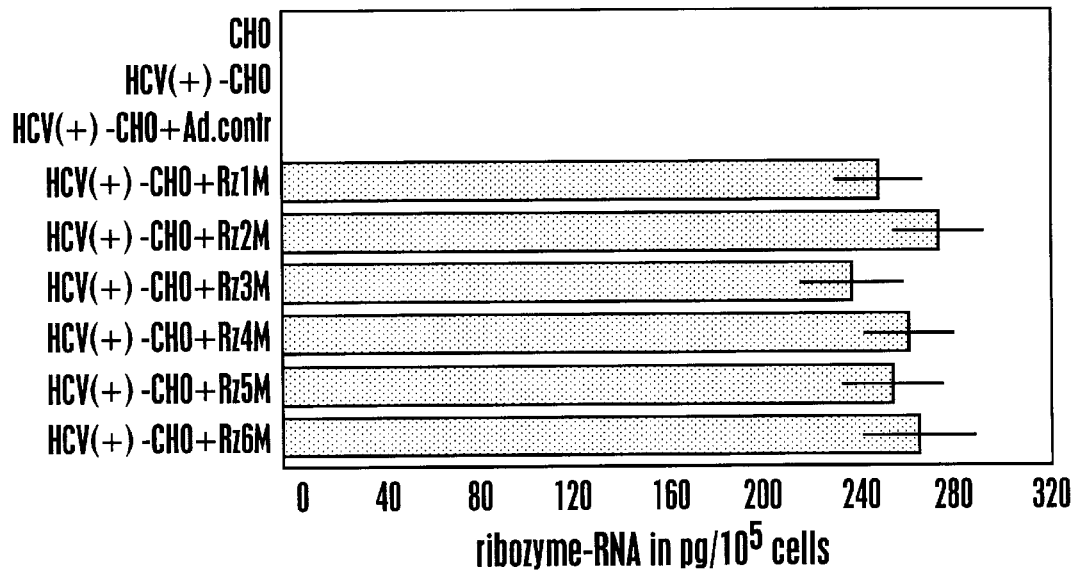
Figure 5C:
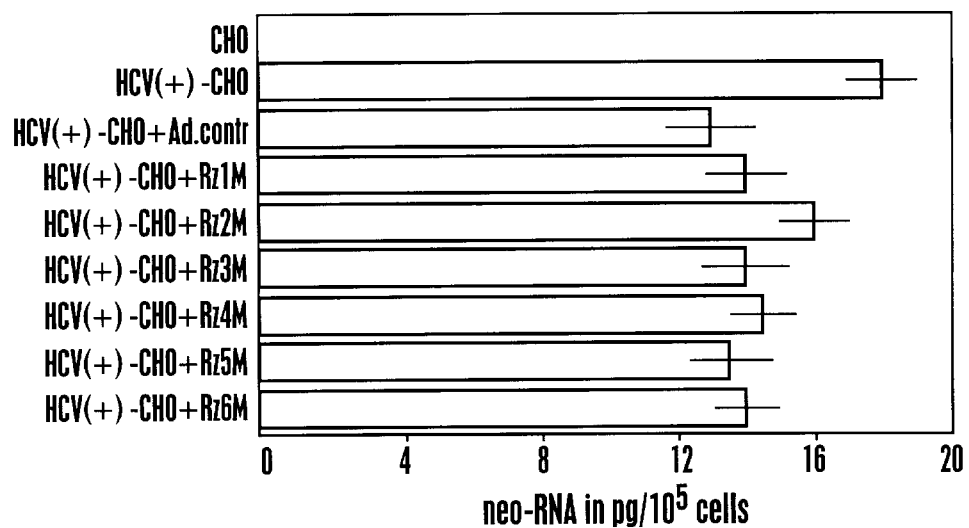
Figure 5D:
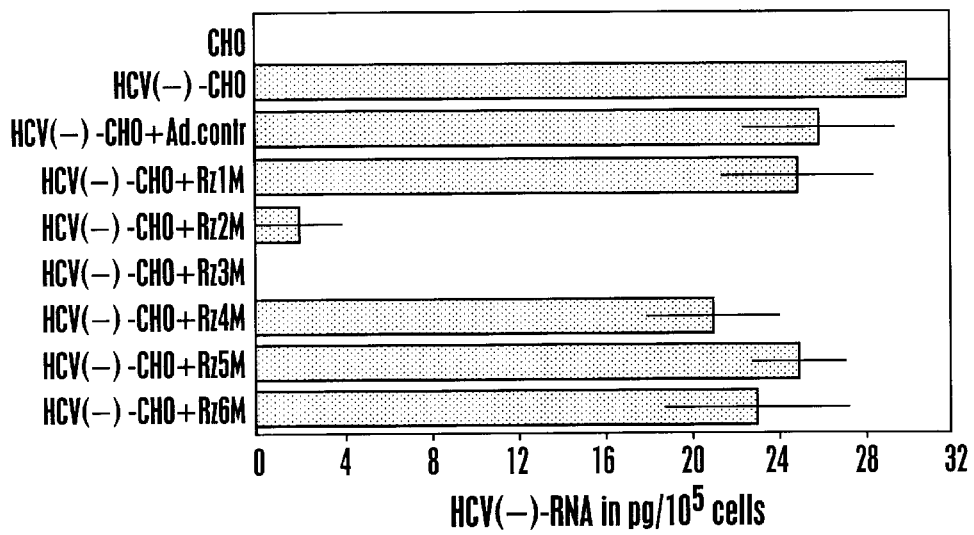
Figure 5E:
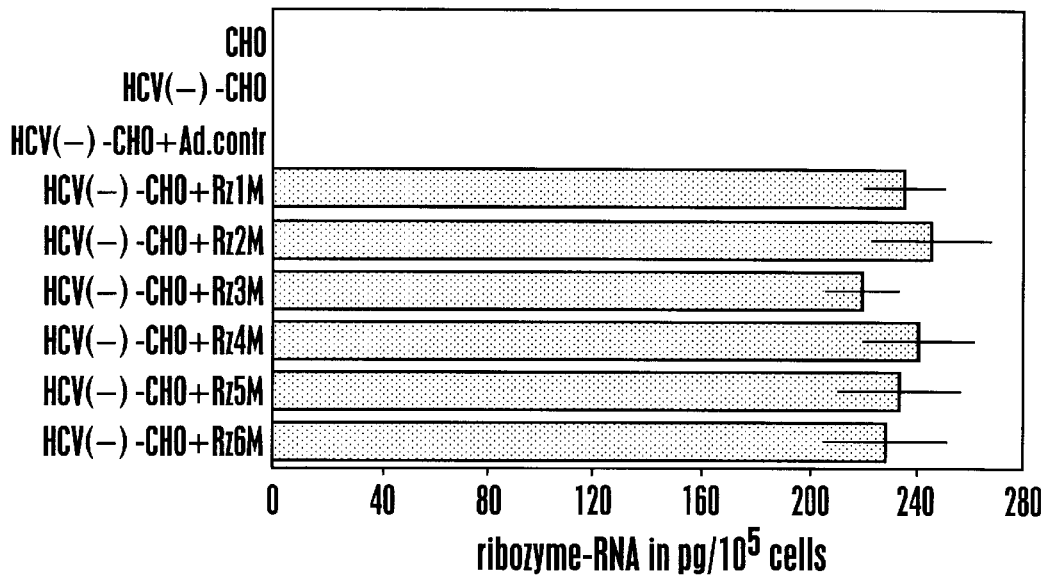

After infection with Ad.contr. a small, non-specific decline in HCV- and neo-RNA was detected, (FIGS. 5A, 5C, 5D and 5F). All the expressed ribozymes directed against the positive strand of HCV RNA (REz 1, 4, 5, 6) reduced HCV (+) RNA in HCV (+) CHO cells (FIGS. 5A and 5B); ribozymes 1 and 4 ablated HCV RNA in these cells. Ribozymes 2 and 3, selected for activity against the HCV minus strand, had no specific effect in HCV (+) CHO cells (FIGS. 5A and 5B) whereas ribozymes directed against the plus strand (Rz 1, 4, 5, 6) did not cleave the minus strand RNA expressed in HCV (-) CHO cells (FIGS. 5D and 5E). Ribozyme 3 eliminated the HCV (-) RNA completely. Fragments after ribozyme cleavage are rapidly degraded and not available for hybridization with the test oligo.

Figure 5F:
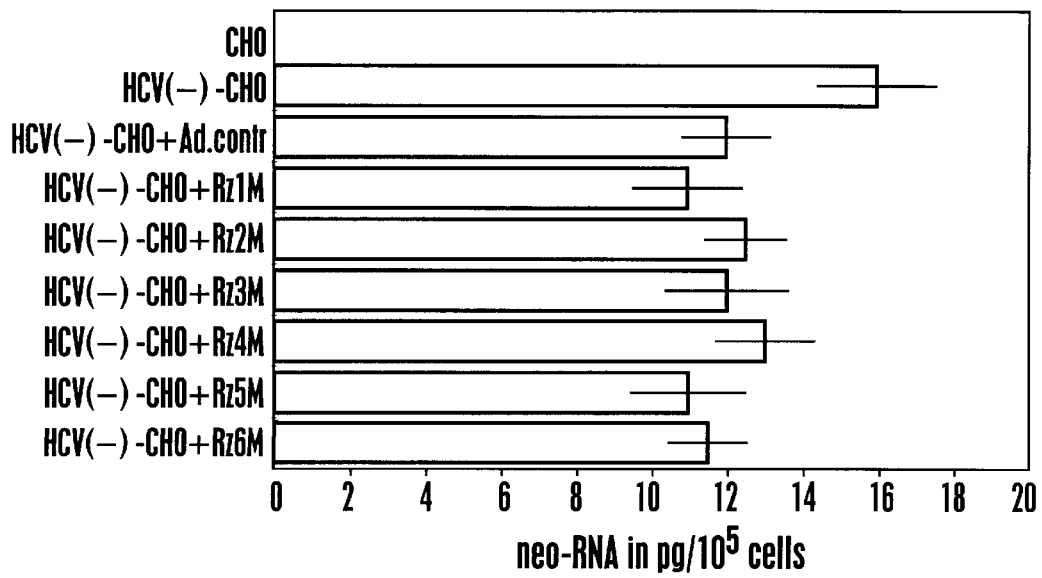

Each of the recombinant adenoviruses expressed about 8000–15,000 ribozyme molecules per cell (FIGS. 5B and 5E). Thus, more than 100-fold excess of ribozymes over the target RNA was achieved, which allowed for the efficient diminution of HCV RNA in CHO cells. The ribozyme effect was specific for HCV RNA because the concentration of neomycin phosphotransferase was not influenced by high ribozyme concentrations (FIGS. 5C and 5F).

EXAMPLE III

Ribozyme-Mediated Inhibition of hGH in Transgenic Animals

This Example shows the adenoviral-mediated targeting and expression of sequence specific ribozymes to liver and the inhibition of expression of the targeted RNA.

Figure 6A:
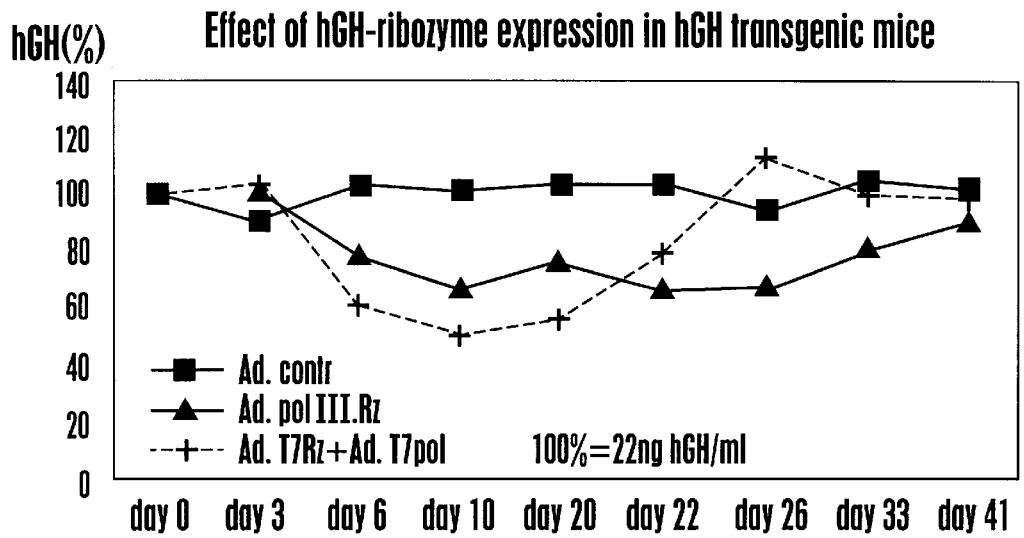
Figure 6B:
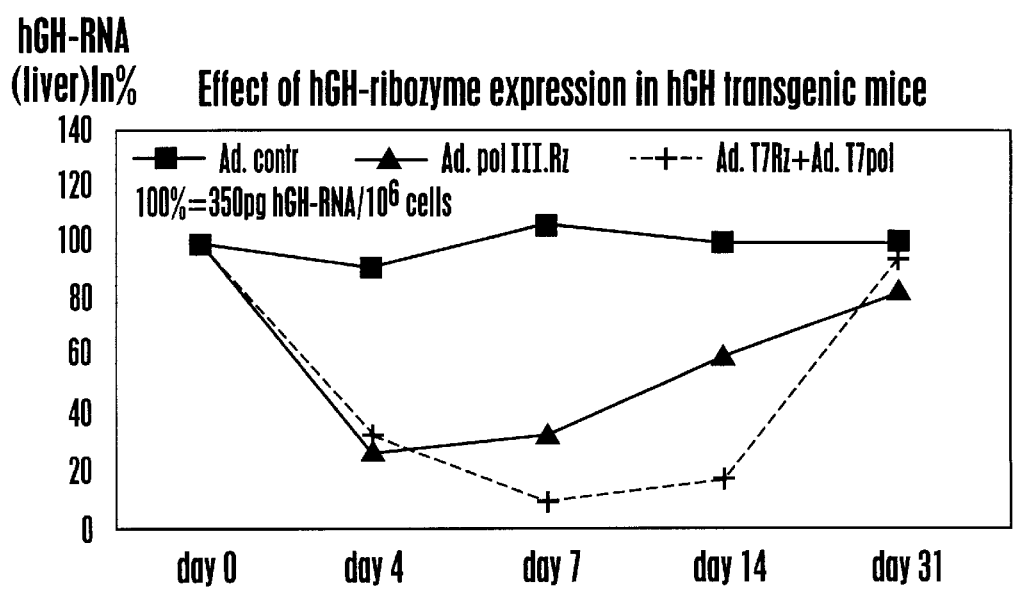

To confirm that sequence specific ribozymes can be targeted to the liver for expression in animals, transgenic mice were created that expressed human growth hormone (hGH) and then treated with adenovirus vectors capable of expressing hGH-specific ribozymes. FIG. 6A shows the concentration of hGH serum concentrations in hGH-transgenic mice after ribozyme therapy, where hGH levels were estimated by enzyme-linked immunosorbent assay (ELISA) as described in Lieber et al., *Meth. Enzymol.* 217:47–66 (1993)). Serum samples were analyzed for growth hormone at varying times after recombinant adenovirus administration. FIG. 6B shows hepatic mRNA quantitation in transgenic mice after ribozyme therapy, where hepatic mRNA levels were determined by solution hybridization (Townes et al., 1985; Durnam and Palmiter, 1983). Ad/RSVhAAT was used as a control vector, Ad.polIII.Rz is adenovirus containing the hGH ribozyme driven by the adenovirus val promoter, and Ad.T7Rz+Ad.T7 pol is a 1:1 mixture of the adenovirus expressing nuclear T7 polymerase from the PGK promoter and an adenovirus containing the T7 promoter used to drive transcription of the hGH ribozyme, (Lieber et al., *Meth. Enzymol.* 217:47–66 (1993)). The effective inhibition of hGH by the adenovirus encoding the hGH-specific ribozyme indicates that HCV-specific ribozymes can also be effective in vivo in inhibiting HCV RNA.

EXAMPLE IV

Inhibition of HCV RNA in Infected Human Hepatocytes

This Example shows the complete elimination of HCV RNA from infected hepatocytes following expression of one or more ribozymes.

The above Examples show the successful selection and use of ribozymes against HCV RNA in both in vitro and in vivo systems. The above Examples also show the successful inhibition of RNA expression in an animal model system. Nevertheless, to further show the effectiveness of the HCV ribozymes, the results of expressing multiple ribozymes specific for either or both of the positive and negative strands of HCV RNA were characterized. For this characterization, and to ensure that secondary factors such as HCV RNA structure, accessibility and localization are similar to that found in an actual infected patient, RNA from freshly isolated hepatocytes of patients with chronic HCV infection was used to test the ribozymes. Two studies were performed which are described below.

Briefly, human liver specimens were obtained from HCV infected liver transplant recipients with end-stage liver disease. An 3×3×2 cm apical piece of the left liver lobe covered from three sites with capsule was perfused for 30 minutes with 120 ml preperfusion solution (Earles balanced salt solution without $Ca^{2+}$) for 20 minutes with collagenase D (Boehringer Mannheim). In comparison to protocols for the isolation of hepatocytes from normal liver a higher collagenase concentration (0.6 mg/ml) was used for the highly fibrotic end-stage liver. Hepatocytes were separated from fibroblasts by three rounds of low speed centrifugation. Up to $5 \times 10^8$ hepatocytes with >50% viability by trypan blue exclusion were obtained and plated at a density of $1 \times 10^7$ on collagen I coated 10 cm dishes in Williams E medium (represses growth of fibroblasts) with 10% FCS. After 5 hours the WE-FCS medium was changed by a hormonally-defined medium (HMD) (Williams E containing 10 µg/ml insulin, 400 ng/ml dexamethasone, 362 ng/ml hydrocortisone, 25 ng/ml human epidermal growth factor, 10 ng/ml human hepatocyte growth factor, 1 mM glutamine and Pen/Strep). The number of plated cells was determined by counting. Plated hepatocytes were infected with adenovirus (moi 200) and collected for RNA extraction after 3 days.

In the first experiment (FIG. 7), hepatocytes were isolated from the explanted liver of a patient infected with HCV genotype 1b as described above. The hepatocytes isolated in culture showed normal morphology. RNA was isolated from hepatocytes and culture media 3 days after infection with a mixture of adenoviruses containing each of the 6 ribozyme genes expressed as a monomer (Ad.Rz1, Ad.Rz2M, Ad.Rz3M, Ad.Rz4M, Ad.Rz5M, and Ad.Rz6M) or Ad.Rz1T–Ad.Rz6T as trimer. The RNAs were quantitatively analyzed for HCV plus and minus RNA, hAAT RNA (as a control for hepatocyte specific mRNAs) and ribozyme RNA concentrations by in solution hybridization.

The results showed that in control hepatocytes, HCV plus strand RNA was detectable at a concentration of about 20 copies per cell although minus strand HCV RNA was undetectable at a sensitivity of less than 1 copy/cell. The amount of minus strand RNA in hepatocytes is thought to be about 1/100 to about 1/1000 that of plus strand RNA (Fong et al., *J. Clin. Invest.* 88:1058–1060 (1991); Wang et al., *J. Infect. Dis.* 166:1167–1169 (1992)). No HCV RNA could be detected in tissue culture supernatants.

Figure 7A:
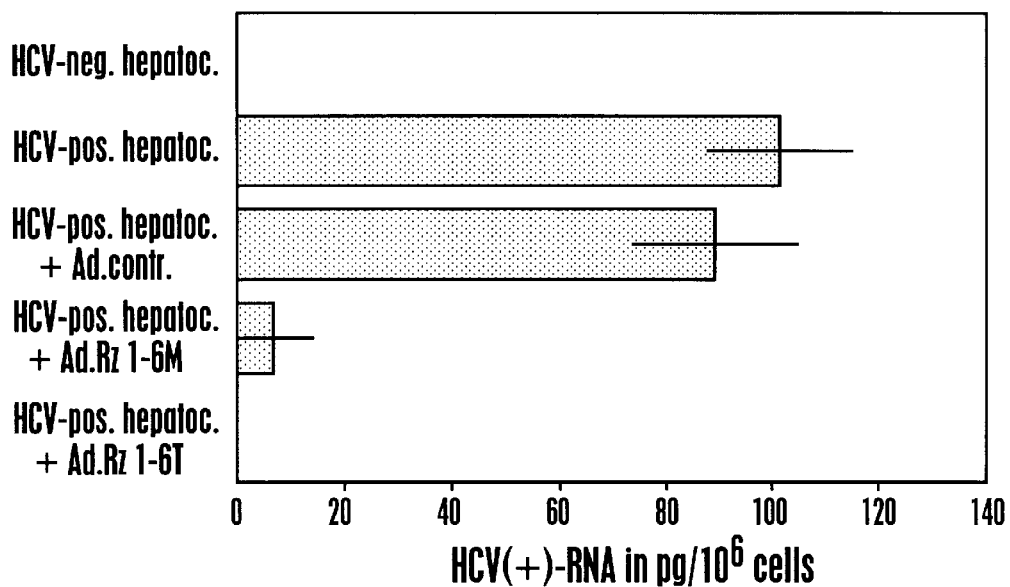
Figure 7B:
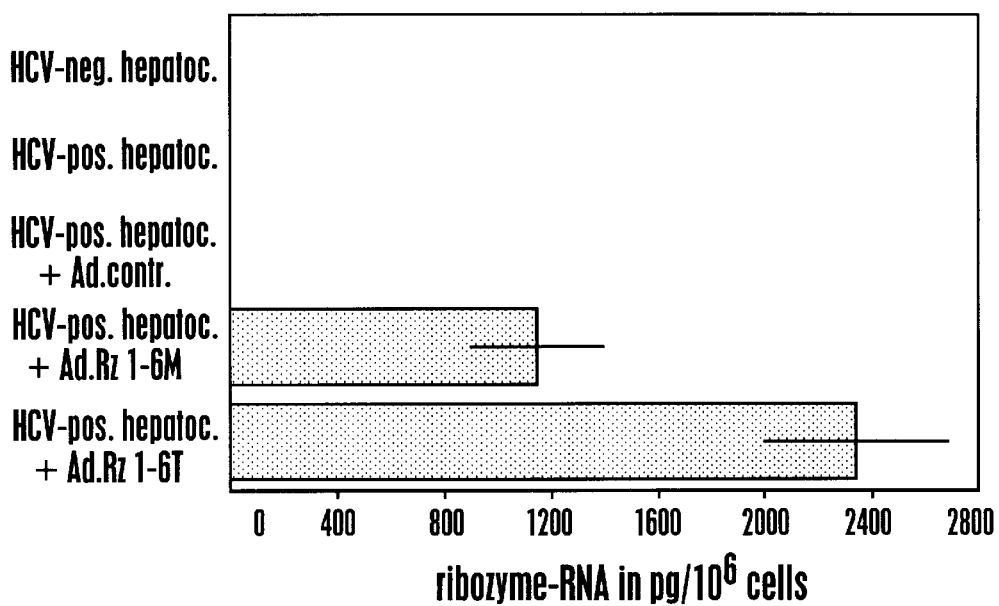
Figure 7C:
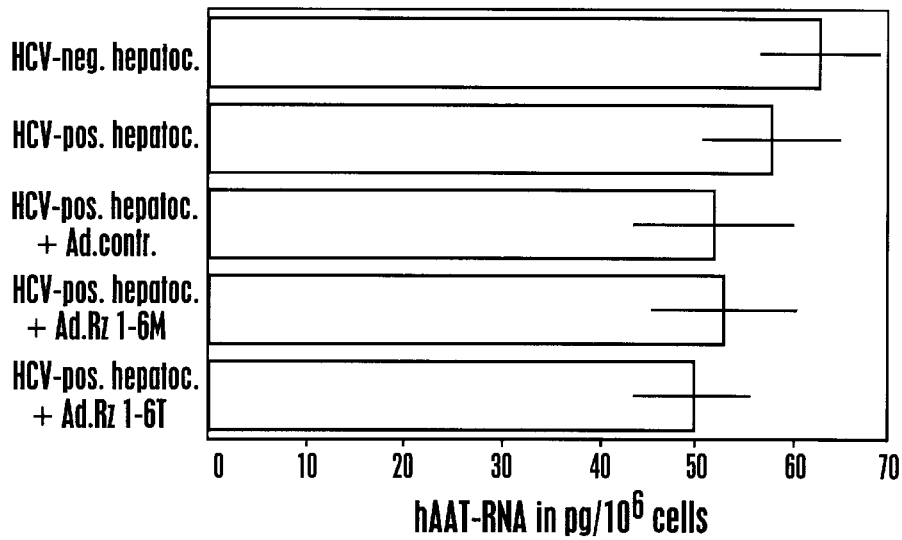

While control adenovirus had a minimal effect on HCV (+) RNA, infection with the adenovirus-ribozyme vectors significantly reduced the HCV RNA concentration. The results of the ribozyme treated hepatocytes are shown in FIGS. 7A and 7B. The mixture of trimeric ribozymes Ad.Rz1T–Ad.Rz6T essentially eliminated all HCV RNA from infected hepatocytes. This result is likely due to a two-fold higher ribozyme level in comparison to the constructs expressing only a single ribozyme (an approximately 700-fold excess over HCV RNA; FIG. 7B). Accordingly, overexpression of any number of ribozymes to achieve this higher ribozyme level is expected to yield similar results.

Figure 8A:
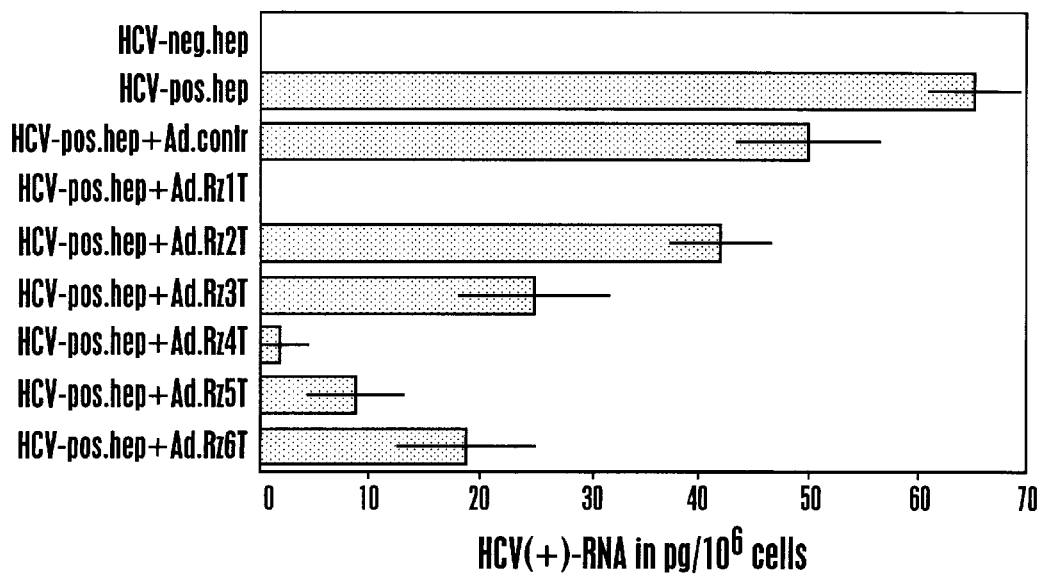
Figure 8B:
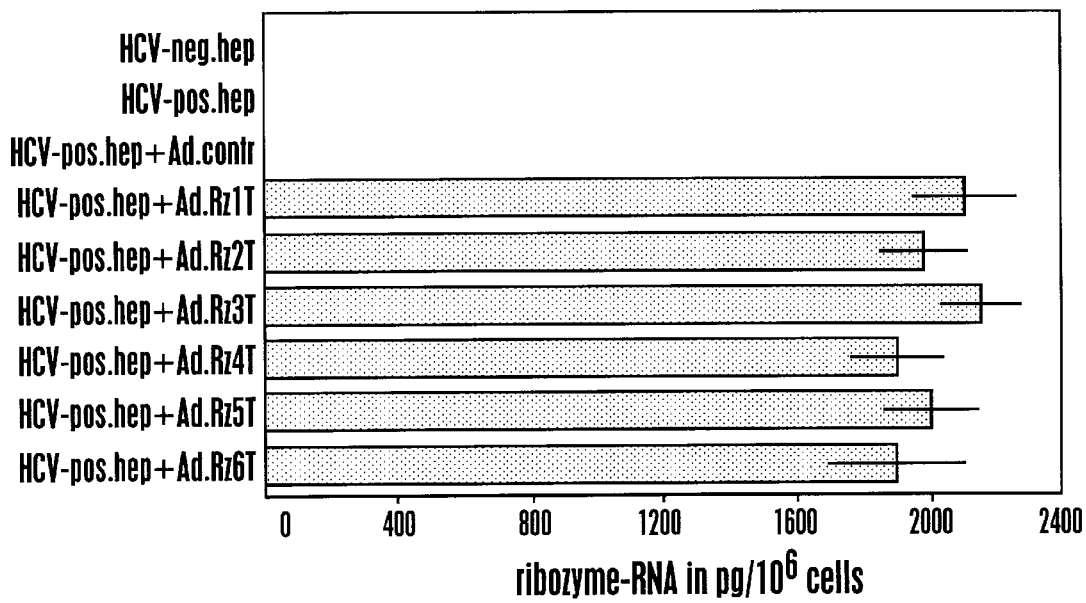
Figure 8C:
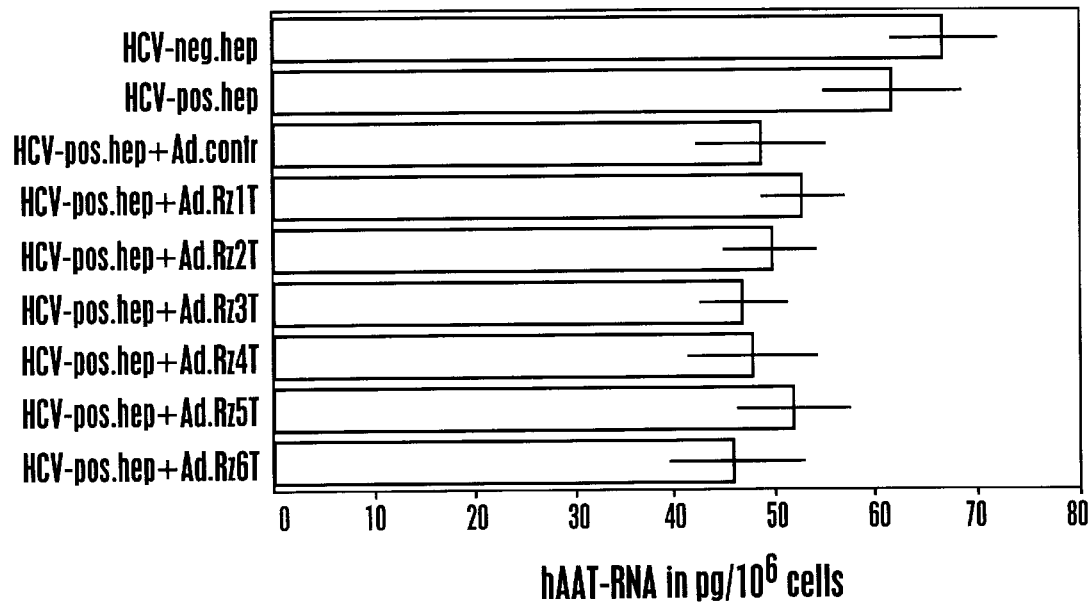

In a second experiment (FIG. 8), hepatocytes from a HCV 1a RNA positive liver were isolated and cultured. Positive HCV RNA (~10 copies/cell) was detected in control hepatocytes. RNA from cultures infected with adenovirus vectors, Ad.Rz1T to Ad.Rz6T were analyzed separately. Among the ribozymes directed against the HCV plus strand, Rz1 and 4 were the most efficient at reducing HCV RNA concentrations (FIG. 8A). Interestingly, ribozymes 2 and 3 against the minus strand reduced the plus strand level as well (FIG. 8A). This result indicates that the plus strand is produced by HCV replication in cells, and cleavage of the minus strand would interrupt this process. The concentrations of expressed ribozymes in the second experiment were similar to the amounts detected in the first experiment described above (FIG. 8B). In both experiments (FIGS. 7C and 8C), the hepatocyte specific HAAT mRNA concentrations were not affected with ribozyme expression.

The above results demonstrate substantial in vivo activity against viral RNAs representing two major HCV genotypes. Moreover, the above ribozyme were not only shown to be effective either singly or in combination, but were also shown to be specific for the target RNA. This specificity offers therapeutic advantages for increasing the efficacy of the treatment and lowering potential side effects of the treatment.

Throughout this application various publications are referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of inhibiting hepatitis C virus RNA replication or expression comprising introducing two or more ribozymes specific for hepatitis C virus RNA into a cell infected with hepatitis C virus, wherein at least one of said ribozymes specifically cleaves hepatitis C RNA in a minus strand hepatitis C virus 5' non-coding sequence.

2. The method of claim 1, wherein said two or more ribozymes specific for hepatitis C virus RNA are introduced into the cell by administering an expression vector encoding said two or more ribozymes specific for hepatitis C virus RNA.

3. The method of claim 1, wherein said two or more ribozymes specific for hepatitis C virus RNA are introduced into the cell via a ribozyme delivery vehicle.

4. The method of claim 3, wherein said delivery vehicle further comprises an adenoviral or retroviral expression vector encoding said two or more ribozymes specific for hepatitis C virus RNA.

5. The method of claim 1, wherein at least one of said ribozymes specific for hepatitis C virus RNA is a hammerhead ribozyme.

6. The method claim 1, wherein a second ribozyme of said two or more ribozymes specific for hepatitis C virus RNA specifically cleaves hepatitis C virus RNA in a HCV 5' non-coding sequence, the capsid sequence, or NS-5 sequence.

7. The method of claim 1, wherein at least one of said two or more ribozymes specific for hepatitis C virus RNA is specific for minus strand hepatitis C virus 5' non-coding sequence and at least one of said two or more ribozymes is from the opposite strand of the virus genome.

8. The method of claim 1, wherein said two or more ribozymes specific for the hepatitis C virus RNA are selected from the group consisting of GCACCATGAGCACGA (SEQ ID NO:2), CCCACAGGACGTCAA (SEQ ID NO: 3), CAACCGTCGCCCACA (SEQ ID NO:4) and TAAACCTCAAAGAAA (SEQ ID NO:5).

9. The method of claim 3, wherein said delivery vehicle further comprises a ligand specific for a receptor on said cells infected with said hepatitis C virus.

10. A method of inhibiting hepatitis C virus RNA replication or expression comprising introducing into a cell infected with hepatitis C virus at least one ribozyme specific for hepatitis C virus selected from the group consisting of GCACCATGAGCACGA (SEQ ID NO:2), CCCACAGGACGTCAA (SEQ ID NO:3), CAACCGTCGCCCACA (SEQ ID NO:4) and TAAACCTCAAAGAAA (SEQ ID NO:5).

11. The method of claim 10, wherein said ribozymes specific for hepatitis C virus RNA are introduced into the cell by administering an expression vector encoding said ribozymes specific for hepatitis C virus RNA.

12. The method of claim 10, wherein said ribozymes specific for hepatitis C virus RNA are introduced into the cell via a ribozyme delivery vehicle.

13. The method of claim 12, wherein said delivery vehicle further comprises an adenoviral or retroviral expression vector encoding said ribozymes specific for hepatitis C virus RNA.

14. The method of claims 12, wherein said delivery vehicle further comprises a ligand specific for a receptor on said cells infected with said hepatitis C virus.

15. A composition for inhibiting hepatitis C virus RNA replication or expression comprising two or more different ribozymes specific for hepatitis C virus RNA, wherein at least one of said ribozymes specifically cleaves hepatitis C RNA in a minus strand hepatitis C virus 5' non-coding sequence.

16. The composition of claim 15, wherein at least one ribozyme is a hammerhead ribozyme.

17. The composition of claim 15, wherein a second ribozyme of said two or more ribozymes specific for hepatitis C virus RNA specifically cleaves hepatitis C virus RNA in a HCV 5' non-coding sequence, the capsid sequence, or NS-5 sequence.

18. The composition of claim 15, wherein at least one of said two or more ribozymes specific for hepatitis C virus RNA is specific for minus strand hepatitis C virus 5' non-coding sequence and at least one of said two or more ribozymes is from the opposite strand of the virus genome.

19. The composition of claim 15, wherein at least one of said two or more ribozymes specific for the hepatitis C virus RNA are selected from the group consisting of GCACCATGAGCACGA (SEQ ID NO:2), CCCACAGGACGTCAA (SEQ ID NO:3), TAAACCTCAAAGAAA GTAAGGTCATCGATA.

20. A method of inhibiting hepatitis C virus RNA replication or expression comprising introducing a ribozyme specific for a minus strand hepatitis C virus 5' non-coding sequence of hepatitis C virus RNA into a cell infected with hepatitis C virus.

21. A composition for inhibiting hepatitis C virus RNA replication or expression comprising a ribozyme specific for hepatitis C virus RNA, wherein said ribozyme is selected from the group consisting of CAACCGTCGCCCACA (SEQ ID NO:4) and TAAACCTCAAAGAAA (SEQ ID NO:5).

22. A method of inhibiting hepatitis C virus RNA replication or expression comprising introducing ex vivo two or more ribozymes specific for hepatitis C virus RNA into a cell infected with hepatitis C virus, wherein at least one of said ribozymes specifically cleaves hepatitis C RNA in a minus strand hepatitis C virus 5' non-coding sequence.

23. The method of claim 22, wherein said two or more ribozymes specific for hepatitis C virus RNA are introduced into the cell by administering an expression vector encoding said two or more ribozymes specific for hepatitis C virus RNA.

24. The method of claim 22, wherein said two or more ribozymes specific for hepatitis C virus RNA are introduced into the cell via a ribozyme delivery vehicle.

25. The method of claim 24, wherein said delivery vehicle further comprises an adenoviral or retroviral expression vector encoding said two or more ribozymes specific for hepatitis C virus RNA.

26. The method of claim 22, wherein at least one of said ribozymes specific for hepatitis C virus RNA is a hammerhead ribozyme.

27. The method claim 22, wherein a second ribozyme of said two or more ribozymes specific for hepatitis C virus RNA specifically cleaves hepatitis C virus RNA in a HCV 5' non-coding sequence, the capsid sequence, or NS-5 sequence.

28. The method of claim 22, wherein at least one of said two or more ribozymes specific for hepatitis C virus RNA is specific for minus strand hepatitis C virus 5' non-coding sequence and at least one of said two or more ribozymes is from the opposite strand of the virus genome.

29. The method of claim 22, wherein said two or more ribozymes specific for the hepatitis C virus RNA are selected from the group consisting of GCACCATGAGCACGA (SEQ ID NO: 2), CCCACAGGACGTCAA (SEQ ID NO: 3), CAACCGTCGCCCACA (SEQ ID NO: 4) and TAAACCTCAAAGAAA (SEQ ID NO: 5).

30. The method of claim 24, wherein said delivery vehicle further comprises a ligand specific for a receptor on said cells infected with said hepatitis C virus.

31. A method of inhibiting hepatitis C virus RNA replication or expression comprising introducing ex vivo into a cell infected with hepatitis C virus at least one ribozyme specific for hepatitis C virus selected from the group consisting of GCACCATGAGCACGA (SEQ ID NO: 2), CCCACAGGACGTCAA (SEQ ID NO: 3), CAACCGTCGCCCACA (SEQ ID NO: 4) and TAAACCTCAAAGAAA (SEQ ID NO: 5).

32. The method of claim 31, wherein said ribozymes specific for hepatitis C virus RNA are introduced into the cell by administering an expression vector encoding said ribozymes specific for hepatitis C virus RNA.

33. The method of claim 31, wherein said ribozymes specific for hepatitis C virus RNA are introduced into the cell via a ribozyme delivery vehicle.

34. The method of claim 33, wherein said delivery vehicle further comprises an adenoviral or retroviral expression vector encoding said ribozymes specific for hepatitis C virus RNA.

35. The method of claims 33, wherein said delivery vehicle further comprises a ligand specific for a receptor on said cells infected with said hepatitis C virus.

36. A method of inhibiting hepatitis C virus RNA replication or expression comprising introducing a ribozyme specific for a minus strand hepatitis C virus 5' non-coding sequence of hepatitis C virus RNA into a cell infected with hepatitis C virus.

37. The method of claim 22, wherein said cells containing ribozymes are administered to an individual infected with hepatitis C virus.

38. The method of claim 31, wherein said cells containing ribozymes are administered to an individual infected with hepatitis C virus.

* * * * *

UNITED STATES PATENT AND TRADEMARK OFFICE
CERTIFICATE OF CORRECTION

PATENT NO.   : 6,107,028
DATED        : August 22, 2000
INVENTOR(S)  : Kay et al.

It is certified that error appears in the above-identified patent and that said Letters Patent is hereby corrected as shown below:

Column 6,
Line 27, please delete "MRNA" and replace therefor with -- mRNA --.

Column 7,
Line 21, please delete "embodiments" and replace therefor with -- embodiment --.

Column 11,
Line 42, please delete "used to as" and replace therefor with -- used as --.

Column 16,
Line 8, please delete "CDNA" and replace therefor with -- cDNA --

Column 17,
Line 54, please delete "Durnham" and replace therefor with -- Durnam --.

Column 19,
Line 29, please delete "An" and replace therefor with -- A --.

Column 20,
Line 45, please delete "ribozyme" and replace therefor with -- ribozymes --.

Column 30,
Line 16, please delete "claims 12," and replace therefor with -- claim 12, --.
Line 41, please delete "TAAACCTCAAAGAAA" and replace therefor with
-- TAAACCTCAAAGAAA (SEQ ID NO:4) and --.
Line 42, please delete "CATCGATA" and replace therefor -- CATCGATA (SEQ ID NO:5) --.

Column 31,
Line 8, please delete "method" and replace therefor with -- method of --.

UNITED STATES PATENT AND TRADEMARK OFFICE
CERTIFICATE OF CORRECTION

PATENT NO.   : 6,107,028
DATED        : August 22, 2000
INVENTOR(S)  : Kay et al.

It is certified that error appears in the above-identified patent and that said Letters Patent is hereby corrected as shown below:

<u>Column 32,</u>
Line 16, please delete "claims 33," and replace therefor with -- claim 33, --.

Signed and Sealed this

Twenty-sixth Day of August, 2003

JAMES E. ROGAN
*Director of the United States Patent and Trademark Office*